(12) United States Patent
Filtvedt et al.

(10) Patent No.: US 7,833,180 B2
(45) Date of Patent: *Nov. 16, 2010

(54) DEVICE FOR APPLYING A PULSATING PRESSURE TO A LOCAL REGION OF THE BODY AND THE APPLICATIONS THEREOF

(75) Inventors: Marius Filtvedt, Nesttun (NO); Erling Bekkestad Rein, Nesoddtangen (NO)

(73) Assignee: Otivio AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/248,616

(22) Filed: Oct. 9, 2008

(65) Prior Publication Data

US 2009/0036959 A1 Feb. 5, 2009

Related U.S. Application Data

(63) Continuation of application No. 10/749,150, filed on Dec. 30, 2003.

(51) Int. Cl.
*A61H 7/00* (2006.01)
(52) U.S. Cl. ........................ 601/151; 601/152
(58) Field of Classification Search ............ 604/6, 604/9, 11, 150–152, 159; 607/104, 108, 607/114; 602/13
See application file for complete search history.

(56) References Cited

U.S. PATENT DOCUMENTS

| | | | |
|---|---|---|---|
| 1,110,494 A | 9/1914 | Kellogg | |
| 1,399,095 A * | 12/1921 | Webb, Sr. ................ | 24/1 |
| 2,113,253 A | 4/1938 | Gray | |
| 2,168,611 A | 8/1939 | Thompson | |
| 2,626,601 A | 1/1953 | Riley | |
| 2,702,552 A * | 2/1955 | Moodie ............... | 607/114 |
| 3,094,983 A * | 6/1963 | MacLeod ............... | 601/9 |
| 3,217,707 A | 11/1965 | Werding | |
| 3,286,711 A * | 11/1966 | MacLeod ............... | 601/11 |
| 3,292,613 A * | 12/1966 | MacLeod ............... | 601/9 |
| 3,403,673 A | 10/1968 | MacLeod | |
| 3,465,748 A * | 9/1969 | Kravchenko ............ | 601/6 |
| 3,565,065 A | 2/1971 | Biggs et al. | |
| 3,757,806 A | 9/1973 | Bhaskar et al. | |
| 3,859,989 A | 1/1975 | Spielberg | |

(Continued)

FOREIGN PATENT DOCUMENTS

EP 1583498 B1 8/2006

(Continued)

OTHER PUBLICATIONS

International Serach Report, dated Jun. 22, 2004 for corresponding PCT Application No. PCT/GB2003/005644 (5 pages).

(Continued)

*Primary Examiner*—Michael A. Brown
(74) *Attorney, Agent, or Firm*—Fredrikson & Byron, P.A.

(57) ABSTRACT

The present invention generally relates to a device for applying a pulsating pressure to a local region of the body and applications thereof. The device may be used to increase the blood flow in a local region of the body, and in preferred embodiments provides a device for regulating the core body temperature of a patient.

11 Claims, 14 Drawing Sheets

U.S. PATENT DOCUMENTS

| | | | |
|---|---|---|---|
| 3,878,839 A * | 4/1975 | Norton et al. | 601/152 |
| 3,896,794 A * | 7/1975 | McGrath | 601/152 |
| 3,977,396 A | 8/1976 | Cartier | |
| 4,149,529 A | 4/1979 | Copeland et al. | |
| 4,186,732 A * | 2/1980 | Christoffel | 601/150 |
| 4,269,175 A | 5/1981 | Dillon | |
| 4,343,302 A | 8/1982 | Dillon | |
| 4,376,437 A | 3/1983 | Sundheim et al. | |
| 4,648,392 A | 3/1987 | Cartier et al. | |
| 4,945,901 A | 8/1990 | Burcke | |
| 5,063,910 A * | 11/1991 | Cartier | 601/159 |
| 5,074,285 A | 12/1991 | Wright | |
| 5,241,958 A | 9/1993 | Noeldner | |
| 5,358,467 A | 10/1994 | Milstein et al. | |
| 5,425,742 A | 6/1995 | Joy | |
| 2,272,481 A | 11/1997 | Meadow et al. | |
| 5,683,438 A * | 11/1997 | Grahn | 607/104 |
| 5,688,225 A | 11/1997 | Walker | |
| 5,697,920 A | 12/1997 | Gibbons | |
| 6,027,464 A | 2/2000 | Dahlquist | |
| 6,149,674 A | 11/2000 | Borders | |
| 6,277,052 B1 * | 8/2001 | Howard | 482/4 |
| 6,565,593 B2 * | 5/2003 | Diana | 607/108 |
| 6,656,208 B2 | 12/2003 | Grahn et al. | |
| 6,974,442 B2 | 12/2005 | Grahn et al. | |
| 2005/0027218 A1 | 2/2005 | Filtvedt et al. | |

FOREIGN PATENT DOCUMENTS

| | | |
|---|---|---|
| EP | 1736131 A2 | 12/2006 |
| EP | 1736132 A2 | 12/2006 |
| WO | 9840039 | 9/1998 |
| WO | 0180790 | 11/2001 |
| WO | 03045289 | 6/2003 |

OTHER PUBLICATIONS

European Search Report, dated Aug. 29, 2008 for corresponding European Application No. 06016769.9 (9 pages).
European Search Report, dated Aug. 29, 2008 for corresponding European Application No. 06016917.4 (9 pages).

* cited by examiner

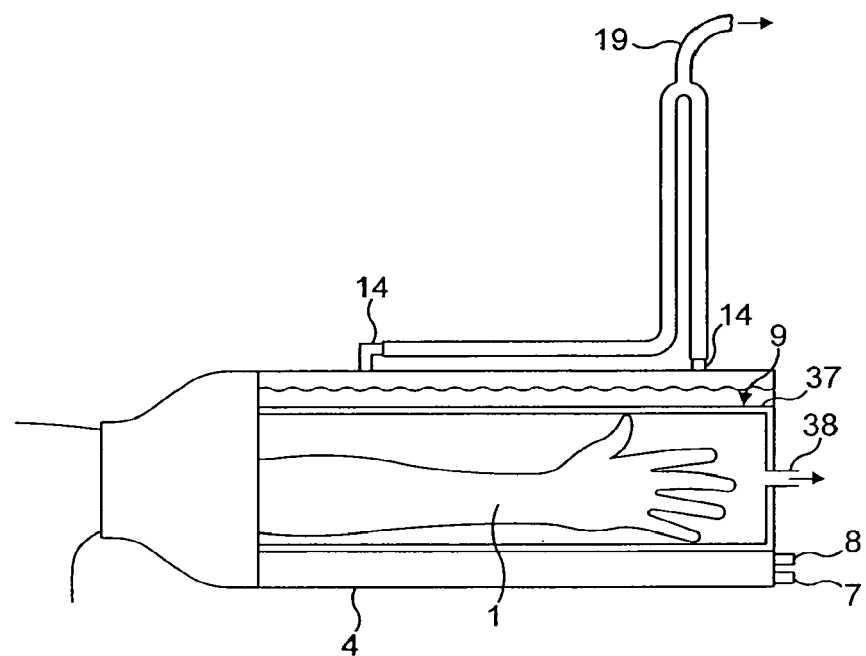
FIG. 9
FIG. 10
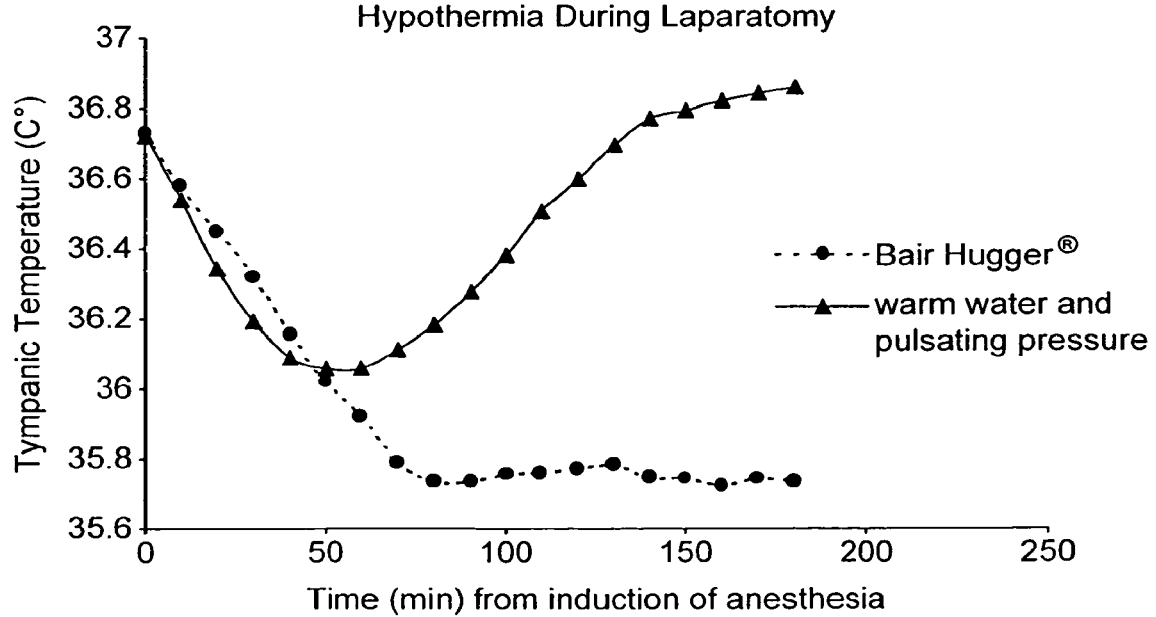

DEVICE FOR APPLYING A PULSATING PRESSURE TO A LOCAL REGION OF THE BODY AND THE APPLICATIONS THEREOF

CROSS REFERENCE TO RELATED APPLICATION

The present application is a continuation of U.S. patent application Ser. No. 10/749,150 filed on Dec. 30, 2003, the contents of which are hereby incorporated by reference in their entirety.

FIELD OF THE INVENTION

The present specification relates to a device for applying a pulsating pressure to a local region of the body and applications thereof. The device may be used to increase the blood flow in a local region of the body, and in preferred embodiments provides a device for regulating the core body temperature of a patient.

BACKGROUND OF THE INVENTION

The application of pressure and/or thermal energy is often used to treat various medical conditions.

It is known to treat oedema by applying pressure to the limb with the oedema. For example, it is known to immerse a limb in a chamber filled with mercury in a flexible bag. Pressure is applied via the chamber of mercury to treat the oedema. More recently an improvement to this system was described in U.S. Pat. No. 4,648,392, to reduce the amount of mercury required in the chamber.

The combined application of pressure and temperature is taught in U.S. Pat. No. 5,074,285 for the treatment of sporting injuries such as bruising and muscle stiffness. In that system, thermal sources, which could be hot or cold, are introduced into pockets close to the wearers skin and pressure is applied to a series of air pockets arranged along the limb that are designed to apply a pressure-gradient repeatedly to the limb.

Hypothermia is a condition resulting from a drop in body temperature and varies in degree according to the amount of undercooling. Many methods for treating hypothermia are already known. Generally, these comprise introducing heat into the core of the body by some means to raise the body temperature. Simple treatments can take the form of a warm drink. Sometimes warm air is blown around the body via air blankets. Such a system is already well established in hospitals and marketed under the name Bair Hugger®. The system relies on heating up the periphery of the body and using the patient's blood flow to draw the heat into the core of the body.

One of the first physiological responses of hypothermia is peripheral vasoconstriction which reduces the amount of blood at the periphery of the body. This can make it difficult to introduce heat into the body through the application of heat to the body surface. It is known that vessels, including capillaries, arterioles, arteries, venoles and veins, can be made to vasodilate under conditions of negative pressure. Vasodilated skin regions, particularly on the forearm, can make efficient heat transfer surfaces.

One system that applies negative pressure to a limb to reduce peripheral vasoconstriction whilst warming the periphery of the patient to treat the hypothermia is taught in U.S. Pat. No. 5,683,438 and sold under the mark Thermostat® by Aquarius Medical Corp. In that system, a limb of the patient is placed in a sealed chamber and the pressure inside that chamber is reduced to a negative pressure of between −20 to −80 mmHg (−2.7 to −10.7 kPa). At the same time, thermal energy is delivered to the surface the limb using a thermal blanket, heat lamp or chemical heating elements. Further developments to this system are described in WO-A-01/80790.

SUMMARY OF THE INVENTION

The device of the present invention generally utilizes a liquid to apply a pulsating pressure to a local region of the body, thereby increasing the blood flow in a local region of the body. This can be beneficial in providing therapeutic treatments to a patient that may be suffering from conditions or complications caused by, but not limited to, hypothermia, hyperthermia, stroke, heart attack, other ischemic diseases, neurosurgery, cancer and ulcers. Additionally, the devices of the present invention may provide therapeutic benefits by increasing the distribution of contrast fluid to a local part of the body, increasing venous circulation, increasing lymphatic circulation, changing the pharmacological distribution of drugs systemically and locally because of locally changed blood flow and possibly diffusion, promoting healing of tissues by increased blood flow, increasing antigen-antibody contact through increased blood flow, lymphatic flow and diffusion, increasing the flow of substances between vessels and cells through increased diffusion.

In various embodiments of the present invention the device takes the form of a pressure chamber in to which a limb of the body can be placed to seal it from external conditions. The pressure chamber normally has internal walls which define, at least in part, a vessel for holding a liquid, whereby in use the limb can be immersed in a liquid contained in the pressure chamber. The liquid surrounds and is in contact with the limb with an air gap being present above the liquid in an upper region of the vessel. The device further includes an element which is in communication with the upper region of the vessel for varying the pressure above the liquid so as to generate pulses of pressure within the chamber. The pulses of pressure generated by the change in pressure above the liquid are transmitted to the limb directly via the liquid.

The foregoing and additional advantages and characterizing features of the present invention and the methods of using the devices of the present invention will become increasingly apparent to those of ordinary skill in the art by references to the following detailed description and to the drawings.

BRIEF DESCRIPTION OF THE DRAWINGS

FIG. 9 illustrates an example of a further device which incorporates a barrier layer between the liquid and the patient's skin;

FIG. 10 shows a comparison between the influence the preferred device of the present invention can have on the core body temperature compared to a conventional device during surgery of a patient;

DETAILED DESCRIPTION OF THE INVENTION

Figure 1:
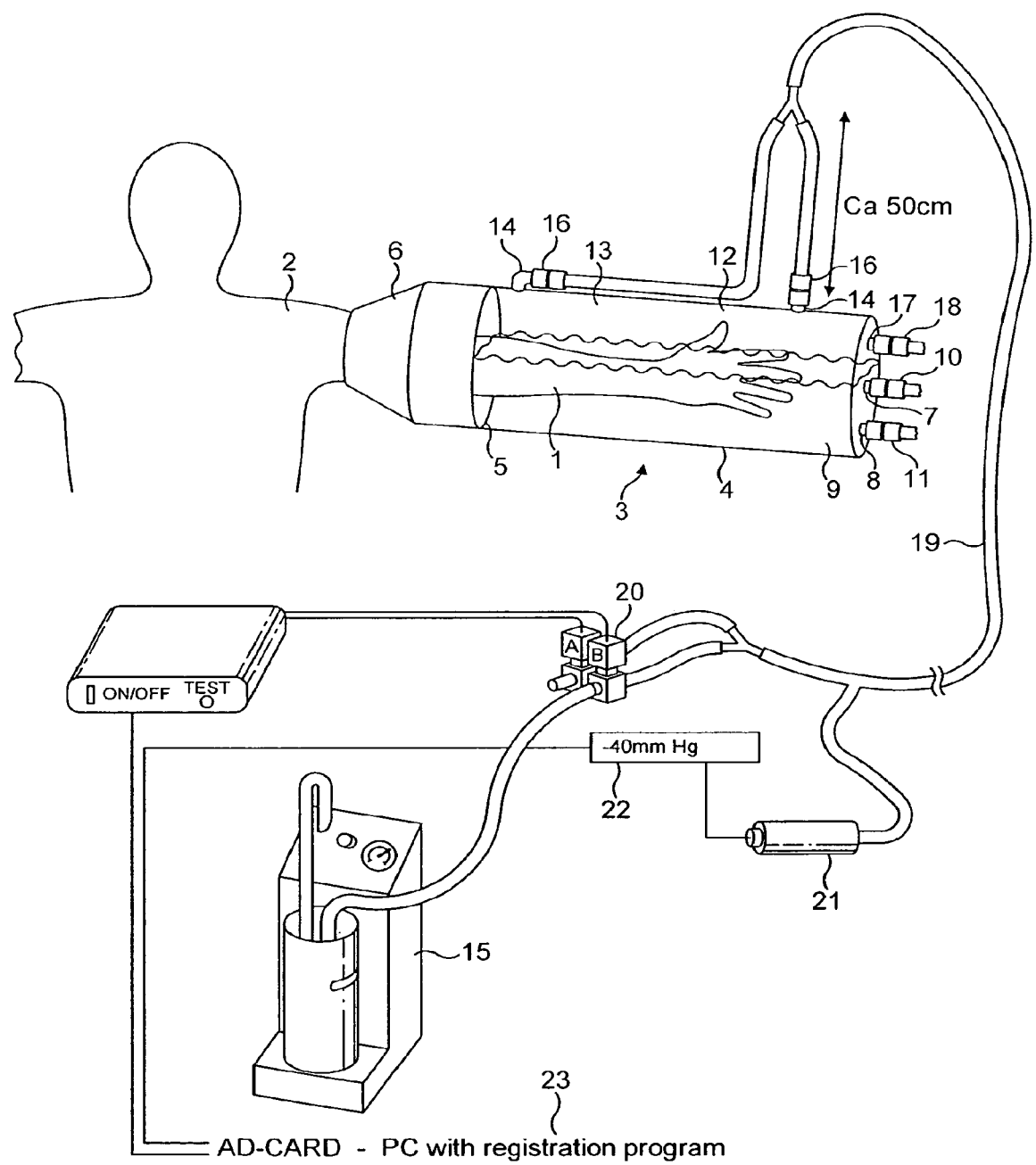
FIG. 1 shows an example of a preferred apparatus for applying a pulsating pressure to a limb.

The devices of the present invention, in broad terms, are generally apparatuses for applying a pulsating pressure to a local region of the body. Various embodiments of these devices take the form of a pressure chamber in to which a limb of the body can be placed to seal it from external conditions. The pressure chamber of these embodiments generally have internal walls which define, at least in part, a vessel for holding a liquid, whereby in use the limb can be immersed in a liquid contained in the pressure chamber such that the liquid surrounds and is in contact with the limb with an air gap being present above the liquid in an upper region of the vessel, wherein an element is provided in communication with the upper region of the vessel for varying the pressure above the liquid so as to generate pulses of pressure within the chamber, and wherein the pulses of pressure are transmitted to the limb via the liquid. In other words these devices are characterized in that the pressure chamber does not contain additional means (e.g., a water perfused mat) to separate the liquid from the surface of the limb. Thus a more simplified construction is possible than that used in the devices of the prior art, thereby reducing manufacturing costs. The vessel walls are preferably the internal walls of the pressure chamber, i.e., the provision of additional liquid containment surfaces or chambers is avoided, keeping the construction of the device simple.

In one embodiment of the present invention, a pulsating negative pressure is generated in the chamber and preferably the pulse frequency is less than the heart beat of the subject. By making the period of the pulses longer than the pulse of the heart, it has been found that circulation can be, improved through the influence of the applied rhythmical pressure. In general the pulses should be longer than one second, preferably of the order of five or more seconds, but preferably less than twenty seconds. It is noted that the period of the pulses can also be varied. In effect the pulsating pressure drives the blood flow in a similar manner to a pump. This may generally be caused by the action of the veins and arteries dilating and constricting at different rates under the application of the varying pressure. A drop in pressure causes local venous pooling of blood which is then forced through the network of veins as the pressure increases, thereby improving local circulation: Thus the present invention provides a device for increasing blood flow in a local region of a body through the application of a pulsating pressure to an area of skin. Other health benefits may also result.

Through the direct contact of the liquid, which is preferably water, there is a good transfer of the pressure pulses to the skin. The invention provides a device that is simple and easy to construct and yet provides improvements over the known devices discussed above in terms of the improved local blood flow that is achievable. The use of liquids, such as water, as a transmitter of the pressure pulses means that the liquid can be in direct contact with the skin without posing undue health risks.

The present invention also extends to a method of operating such a device and to a method of applying a pulsating pressure to a local region of the body, in particular a method of increasing blood flow in a local region of a body, through providing a device as described above having a pressure chamber, introducing a limb into the pressure chamber such that it is sealed from external conditions, filling or partially filling the pressure chamber with a liquid to immerse the limb in the liquid so that it is substantially surrounded by and in contact with the liquid, generating a pulsating pressure within the chamber and transmitting the pulses of pressure to the limb via the liquid. The method has application in medical and non-medical situations.

In many embodiments of the present invention, the liquid is circulated in the device and around the surface of the limb (i.e., in direct contact with the skin). In this way the temperature of the liquid can be adjusted to influence the temperature of the blood in the surface layers of the limb. Circulating the liquid allows the temperature to be controlled accurately.

In accordance with various embodiments, the device of the present invention is in the form of a pressure chamber in which a flow of liquid can be generated. The chamber has an opening for introducing a limb into the chamber for immersing it within the flow of liquid provided in the chamber. In this way the liquid is circulated within the chamber in contact with the surface of the limb. The device is provided with an element or means to generate simultaneously pulses of pressure within the chamber and thereby exert a pulsating pressure on the surface of the limb whilst the limb is immersed in the flow of liquid. In the method described above, the method would also include the step of circulating the liquid within the chamber and around the surface of the limb immersed in the liquid.

More particularly, in various embodiments of the present invention, the pulsating pressure application devices include a housing defining a pressure chamber having walls and an opening for receiving a limb. A seal is provided for sealing the chamber from external conditions, the seal being arranged around the opening for sealing engagement with the limb. A connection may be provided through a wall of the chamber to communicate the chamber with a pressure source that is at a pressure different from atmospheric pressure for regulating the pressure within the chamber. An inlet and outlet may be provided in the housing for introducing and discharging a liquid into and out of the chamber. Preferably the inlet and outlet are in communication with each other via a fluid path that is defined by the internal walls of the chamber and the surface of the limb once it has been introduced into the chamber, such that in use liquid flows from the inlet into the chamber, circulates around and in contact with the surface of the limb and is then discharged via the outlet.

In various embodiments of the present invention, the liquid that is in contact with the skin is at a temperature different to that of the core body temperature. Hence, the liquid is a thermal transfer medium that transfers heat into or out of the body depending on whether it is at a temperature hotter or cooler than the core body temperature respectively. The temperature of the heat transfer medium and the rate of heat transfer may be sufficient to maintain the core body temperature at a particular temperature, e.g., normal body temperature, or within a degree or two either side of the particular temperature. The temperature of the heat transfer medium and the rate of heat transfer may also be greater so as to effect a change in the core body temperature of the subject, e.g., a patient.

Thus there is also provided a method and apparatus for regulating the core body temperature comprising the simultaneous application of a thermal energy transfer medium and a pulsating pressure to a portion of skin on a body, wherein the thermal energy transfer medium is a liquid and the liquid is in direct contact with the skin. The pulsating pressure is applied to the skin by a device described above in accordance with the present invention. Core body temperature regulation may be useful in non-medical as well as medical applications.

Numerous advantages are achieved through this device. The construction is far simpler than for known devices that aim to regulate the core body temperature. There is better thermal energy transfer from the liquid to the surface of the limb because it is in direct contact and because there is greater heat transfer surface area. The device is easier to fit than the known devices because, for example, there is no thermal blanket within the pressure chamber. The device can also be used on an arm or a leg without the need for different shapes and sizes of thermal blanket. The device of the present invention is therefore far more accommodating for use on different limbs and size of limb than the known arrangements. A single device can be used for different applications reducing equipment costs and storage issues.

The present invention provides therapeutic benefits in a number of different manners and/or applications. For example, the devices of the present invention can be utilized to enhance and maximize thermal energy transfer to or from the patient's limb. The direct contact of the limb with the liquid increases the rate of energy transfer to or from the liquid to the limb. Generally, the rates of thermal energy transfer are proportional to the surface area in which transfer takes place. By immersing the entire limb in the liquid, the surface area in which heat transfer takes place is maximized.

The circulation of the liquid around the surfaces of the limb also improves the thermal energy transfer between the liquid and the limb. First, the circulation allows for precise temperature control. The liquid being introduced into the chamber and circulated can be maintained at a precise temperature.

The circulation also allows for forced convection to take place. Forced convection allows for better energy transfer as compared to methods using conduction (e.g., placing a limb in contact with a heated water mattress) or using natural convection (e.g., immersing a limb in a still body of heated water). Conduction takes place when energy is transferred to or from one still material in direct contact with another still material. For example, if a limb were placed in direct contact with a heated water mattress, heat would be transferred from the water mattress to the limb. Natural convection takes place when energy is mass transferred to or from one large mass to a surrounding ambient medium (such as air or water). For example, if a limb were immersed in a body of still heated water, heat would be transferred from the body of water to the limb. Forced convection takes place when energy is transferred to or from one large mass to a surrounding moving medium (such as air or water). Forced convection is used in the present invention when a limb is placed in a body of heated water that is circulating around the surfaces of the limb. Forced convection allows for maximum heat transfer in comparison to prior methods using conduction or natural convection.

Likewise, a liquid medium allows for better thermal energy transfer than an air medium. Mediums having a higher thermal conductivity and specific heat allow for better heat transfer than other mediums. The thermal conductivity and the specific heat of water are approximately 100-200 times greater than in air. Thus, the present invention transfers energy much better than forced air and other methods. Thus, by circulating a liquid rather than air, energy transfer is maximized.

The devices of the present invention also increase local blood velocity by application of pulsating negative pressure to the limb. Pulsating negative pressure increases the blood velocity in the limb much better than constant, negative alone. The increase in blood velocity is advantageous because the blood warmed in the limb can be quickly transferred from the limb to the remaining body.

The thermal energy transfer medium in various embodiments of the present invention is a liquid and is preferably water since it is cheap, non-toxic and has a high specific heat capacity. In use the water may cause wrinkling of the skin, but the benefits of the system far outweigh this slight disadvantage. The wrinkling disappears minutes after the water is removed. Some patients reported improvement of their skin condition after being treated with the device. None reported negative effects.

The water can include additives to minimise this effect and to reduce the discomfort to the patient, e.g., painkillers or local anaesthetic agent. Additives may be chosen to reduce shivering or to encourage vasodilation in the blood vessels. These could be given systemically or locally, and could be administered before or simultaneously with the invention, for example, intravenously, intra-artery, oral, rectal, etc. In the most preferred embodiments, painkillers or local or regional anaesthetics are administered prior to the limb being inserted into the chamber.

Viewed from another aspect, in broad terms the present invention provides a method of transferring thermal energy to or from a body comprising introducing a limb of a patient into a flow of liquid which is at a temperature different to that of the core body temperature of the patient whilst simultaneously applying a pulsating pressure to the surface of the limb being exposed to the flow of liquid.

Thus, in one embodiment, the present invention provides a method of transferring thermal energy to or from a body. The method of thermal energy transfer generally includes providing the device of the present invention for applying pulsating pressure to a limb. As previously suggested, an embodiment of such a device includes a chamber having a seal, a connection communicating the chamber to a pressure source that is at a pressure different from atmospheric pressure, and a liquid inlet and outlet. Next, a limb is introduced into the chamber and the seal seals against the limb to provide an enclosed environment. Once the limb is sealed in the chamber, a liquid is introduced into the chamber via the inlet and later discharged via the outlet. The liquid follows a fluid path defined by the walls of the chamber and the surface of the limb such that the liquid is circulated around, comes in contact with the surface of the limb and simultaneously generates pulses of pressure within the chamber.

The present invention also provides a method of applying a pulsating negative pressure to a local region of the body to provide therapeutic treatments. These treatments can be administered to a subject by first providing a pressure chamber. Next a limb may be introduced into the pressure chamber such that the limb is sealed from external conditions. Once the limb is sealed in the chamber, a liquid may be introduced into the pressure chamber so that the limb is substantially surrounded by and in direct contact with the liquid. Finally, negative pressure is alternately generated and released within the chamber, thereby transmitting to the limb the negative pressure through direct contact with the liquid.

The alternately generated and released negative pressure normally comprises alternately generating negative pressure for a predetermined time interval and releasing the negative pressure for a predetermined time interval. For example, the alternately generating and releasing negative pressure within the chamber comprises alternately generating negative pressure for a time interval of between about 1 and 20 seconds, preferably about 5 and 15 seconds, and releasing the negative pressure for a time interval of between about 2 and 15 seconds, preferably about 5 and 10 seconds. In particularly preferred embodiments, the alternately generating and releasing negative pressure within the chamber comprises alternately generating negative pressure for a time interval of about 10 seconds and releasing the negative pressure for a time interval of about 7 seconds.

Likewise, the alternately generating and releasing negative pressure within the chamber preferably comprises alternately generating a negative pressure between about −10 mmHg and −120 mmHg, preferably −20 mmHg and −80 mmHg, and releasing the negative pressure. For example, in preferred embodiments, the alternately generating and releasing pulses of negative pressure within the chamber comprises alternately generating a negative pressure of about 40 mmHg and releasing the negative pressure.

The liquid introduced into the pressure chamber of the devices of the present invention generally comprises one or more liquids having a temperature different than the core body temperature. For example, water having a temperature different than the core body temperature may be utilized in the device of the present invention. In certain embodiments, the method further comprises circulating the liquid around the surfaces of the limb to transfer heat to or from the limb. The method may also further comprise administering an anesthetic to the limb prior to introducing the limb into the pressure chamber.

An additional method of the present invention also includes a method of applying a pulsating negative pressure to a local region of the body. This method also comprises providing a pressure chamber containing a gas. Once the chamber containing a gas is provided, a limb may be introduced into the pressure chamber such that the limb is sealed from external conditions. Next, the pressure chamber is partially filled with a liquid so that the limb is substantially surrounded by and in direct contact with the liquid while leaving a gas pocket above the liquid in an upper region of the chamber. The gas pocket is then continuously supplied a constant negative pressure followed by the introduction of a positive pressure into the gas pocket at predetermined time intervals to temporarily release the negative pressure within the chamber.

The present invention further provides a method of transferring thermal energy to and from a body. For example thermal energy is transferred to and from the body by first providing an enclosure. Next a limb is introduced into the enclosure such that the limb is sealed from external conditions. Once the limb is sealed from external conditions in the chamber a thermal exchange liquid is placed into the chamber so that the limb is completely surrounded by and in direct contact with the liquid. The introduced thermal exchange liquid will generally have a predetermined temperature different than the core body temperature. Next, the introduced thermal exchange liquid is circulated around the surfaces of the limb, the liquid thereby transmitting heat to or from the limb. A pulsating negative pressure is then generated within the enclosure, thereby transmitting the pulsating negative pressure to the limb through direct contact with the liquid. Finally, the circulated thermal exchange liquid may be discharged from the enclosure.

Additionally, the devices of the present invention further provides a method of treating hypothermia in a patient's body. The method of treating hypothermia generally comprises introducing a limb into a pressure chamber such that the limb is sealed from external conditions. Once the limb is sealed in the pressure chamber a thermal exchange liquid is introduced into the pressure chamber to immerse the limb in the liquid so that the limb is substantially surrounded by and in contact with the liquid. The thermal exchange liquid normally has a temperature warmer than the core body temperature so that the heat in the liquid is transmitted to the limb. Next, negative pressure is alternately generated between about −10 mmHg and −120 mmHg, preferably about −20 mmHg and −80 mmHg, within the chamber for a time interval of between about 1 and 20 seconds, preferably about 5 and 15 seconds, and releasing the negative pressure for a time interval of between about 2 and 15, preferably about 5 and 10 seconds.

The effects of the pulsating pressure, at least in one preferred embodiment, are believed to be as follows. Firstly a negative pressure is generated leading to an increase in transmurale pressure. This leads to a mechanical local dilatation of the vessels because of the drop in pressure. The veins are then dilated more than the arteries due to the greater elastic nature of the walls. Within a few seconds the negative pressure leads to a local venous pooling of blood. During this period the blood flow also increases in the arteries due to dilatation. The pooling of blood is believed to be present in all layers (plexus) from the subcutaneous to the more central veins. The pooling of blood in the veins brings more blood closer to the surface of the skin, and thereby makes it more accessible to heat transfer (gain/loss). Returning the blood through more peripheral veins reduces the heat exchange between supplying arteries and returning veins, the counter current effect. When the pressure drops back to zero (relative to atmospheric pressure), the veins constrict and the blood is forced towards the direction with the lowest resistance to flow. The venous valves will effectively force the blood in the direction towards the heart only. If a positive pressure is added the transmurale pressure will drop. The intramural pressure is much larger in the arteries. This leads to a relative larger constriction of veins compared to arteries, and the veins are "emptied" of blood. The veins are now ready to receive more blood, and the pressure starts to drop again. The microvasculature capillaries also appear to be affected and there is also a possibility that the lymphatic system is affected too, and that lymph flow is increased. Lymphatic circulation is believed to be affected by the pulsating pressure in the same way as the veins because the vessels also have one-way valves. As the vessel walls are even thinner than in the veins, a system operating on the lymphatic system alone may be utilised by operating at lower pressures (including positive pressures) but following the same pulsating mode, thereby minimizing the effects on the arteries/veins (because increased blood flow can have a negative effect on oedema etc.). An example of this may be to apply pulses with 15 seconds on and 15 seconds off at less than 20 mmHg (2.7 kPa).

Using an ultrasound Doppler measuring technique, it has been found that a preferred embodiment can improve blood velocity by up to at least 30% in the brachial artery. In experiments, an average of at least 50% increase in blood velocity and an increase of 200% in a single subject have been witnessed. By pulsating the pressure, it is believed to facilitate the immediate and repeated increase of blood velocity without inducing a reflex constriction as a result of the venus pooling. This is an effect that appears to occur with the known constant negative pressure arrangements. The reflex is more pronounced in the legs, probably because it acts as a means of preventing pooling of blood when standing. Under constant negative pressures of −40 mm Hg (−5.3 kPa) it was found that blood flow decreased by up to 20%. This is probably due to the veino-arterial reflex that is elicited when the veins are distended. Receptors in the walls of the veins sense the dilation, and through a spinal reflex arch the supplying arterioles are constricted. In the present invention, the pulsating of the pressure tends to prevent this, and the blood flow is instead increased. Without any pharmacological or other blocking agent, the invention has been found to work best on the arms because of the reduced reflex constriction effect. Where blocking or reducing of the reflex is possible in the legs, a better circulation may be achieved than in the arms and there is also a greater total area of heat transfer to benefit from.

The increase in blood flow is dependent on the patient's thermal state. If the patient is cold, the vessels of the skin are constricted to eliminate heat loss. The subcutaneous adipose tissue is also an effective insulator. In this way heat transfer (gain/loss) through the skin is limited. Under these conditions, the present invention can be very effective. The vessels are "forced" to circulate blood and heat exchange with the heat transfer medium can be effectively restored.

In a warm state, the vessels are already dilated. In this situation the potential to increase the flow may be reduced. However, the application of a positive pressure may help the veins to empty blood to the heart. If cold water is applied locally to cool down a warm patient, there is a tendency for the blood vessels to constrict. A pulsating pressure will keep the vessels open, and help with the effective transfer of heat away from the body.

The locally applied heat affects the circulation locally. Cold water can constrict vessels locally ands warm water can dilate vessels. This can sometimes work to the disadvantage of the patient. By applying a pulsating pressure the circulation can be "forced" through, whilst the skin works as a thermal energy transfer surface, e.g., as a radiator.

The increased blood flow can be utilised in many different ways. The potential applications of the invention are numerous. The invention may be used in connection with several important clinical problems listed below:

Prevention of hypothermia by heat transfer to the body (heat gain)
Treatment of hypothermia by heat transfer to the body (heat gain)
Prevention of hyperthermia by heat transfer from the body (heat loss)
Treatment of hyperthermia by heat transfer from the body (heat loss)
To induce hypothermia to treat stroke patients, heart attack and other ischemic diseases, for neuro surgery etc.
To induce hyperthermia to treat cancer patients globally and locally
Treatment of ulcers that has difficulties to grow by increasing blood flow locally (leg ulcers)
Changing the pharmacological distribution of drugs systemically and locally because of locally changed blood flow and possibly diffusion
Increasing the distribution of contrast fluid to a local part of the body
Increasing venous circulation
Increasing lymphatic circulation
Promoting healing of tissues by increased blood flow
Increasing antigen-antibody contact through increased blood flow, lymphatic flow and diffusion
Increased flow of substances between vessels and cells through increased diffusion.

The physiological effects on the body of negative pressure has been the subject of research with the main conclusions that 90% of the negative pressure is distributed to the underlying tissue with increased transmurale pressure and dilatation of vessels and changes in venous and arterial circulation.

The reference to a "limb" used herein should be interpreted as being any part of a human or animal body that can be easily introduced into the device, for example, an arm or leg or portion of an arm or leg, e.g., forearm, hand, lower leg, foot, or possibly even more than one of such parts of the body if the situation allows. In certain situations it may be preferable to use, more than one device to increase the amount of heat transfer. For transferring thermal energy to or from the patient, the greater the surface area of skin contact and the more efficient that area of skin is at transferring thermal energy from or to the patient's blood, and hence the core of the patient, the better. For this reason, it is preferred to use the patient's forearm in the device. There is also less reflex constriction in the forearm than the leg of a patient, leading to improved thermal energy transfer. Where maximum heat transfer is required, the device should be large enough to accommodate the whole arm or at least as far up the upper arm as possible, e.g., the middle of the upper arm. The seal, e.g., a sealing cuff, preferably fits above the elbow around the patient's biceps and triceps with the rest of the arm and hand extending into the device. Not only does this maximise the surface area of skin exposed to the liquid but it also means that the blood will be flowing in the distended venous plexus in close proximity to the liquid for longer as it flows through the upper arm, forearm and hand. In this way therefore, the volume of blood and the rate of blood flow are both maximised.

Where the device is being used to transfer only small amounts of thermal energy, for example, warming of the body in preparation for a sporting activity, cooling of a body on a hot day or warming on a cold day for comfort, etc., a smaller thermal energy transfer area, such as just the hand or foot, may be sufficient. The device could take the form of a mitten or boot, for example. Thus, for applications, say, where a lesser extent of heat transfer is required, the sealing cuff may seal closer to the end of the limb or perhaps even a second seal may be provided for the hand or foot to be external of the device once the arm or leg is in place.

Access and heat transfer requirement will largely dictate where the device can be applied on the body. If an operation is being perforated on the top part of the body, then it may be preferable to use the device on the patient's leg so that the device is out of the way of the surgeon. However, in order for the device to work effectively, particularly in the treatment and prevention of hypothermia, it must be able to transfer heat to or from the patient at a rate which is faster than the patient can lose or generate heat through normal biological processes. From preliminary studies, it has been found that this cannot always be achieved in a healthy normal person using a device enclosing just the lower leg and foot although some benefit may be achieved in certain situations. In theory it is also conceivable that a device of an appropriate size and having an appropriate seal could receive two legs of a patient to maximise thermal energy transfer.

In use, a pocket of air remains above the surface of the liquid in the chamber. Pressure within the chamber is varied by altering the pressure of the air in this air pocket. The pressure and the changes in the pressure within the chamber are transferred to the surface of the limb via the liquid.

The reference to "air" used herein as a pressure regulating medium is in no way intended to limit the invention to devices that just use air. Other gases, for example, inert gases, would also be suitable although would add considerably to the costs of operating the device.

Preferably the gas is air and the pressure source is a vacuum line, which are commonplace in hospitals. Where only compressed air is available, a converter can be used to convert this to a source of negative pressure. Such pressure sources are at substantially constant pressure and therefore a regulating device needs to be provided to generate a pulsating pressure. A pump could provide the pulses of pressure directly or could be used in conjunction with a regulating device to generate the pressure pulses. Where the device is being used in a non-hospital environment, for example, as part of rescue equipment, then it may be necessary to use a pump, which may have its own power source or be operated manually. Circulation of the liquid could be achieved via a stirrer located in the chamber.

Preferably the pressure source is at a pressure below atmospheric pressure, thereby causing a drop in the pressure within the chamber to apply a negative pressure (i.e., the amount of pressure below atmospheric pressure) to the limb. The chamber should be configured to withstand negative pressures of at least −80 mmHg (−10.7 kPa), preferably considerably more. That is to say that a negative pressure of −80 mmHg (−10.7 kPa) within the chamber would correspond with an internal pressure of 680 mmHg (90.7 kPa) based on the standard value for atmospheric pressure of 760 mmHg (101.3 kPa).

Preferably the pressure source is at a negative pressure of −80 mmHg (−10.7 kPa), more preferably −60 mm Hg (−8.0 kPa) or less and most preferably is at around −40 mmHg (−5.3 kPa) in order to reduce the possible complications that are thought to arise from the application of higher negative pressures. The purpose of the negative pressure is to encourage local vasodilation in the surface of the limb, so the negative pressure should be chosen to maximise this whilst minimising the risk of possible complications. Pulsating the negative pressure has been found to encourage blood flow and for this reason a pulsating negative pressure of 0 to −40 mmHg (0 to −5.3 kPa) is preferably generated in the chamber.

Preferably the pressure source is at a constant pressure, preferably a constant negative pressure, and air is bled into the chamber via a valve to return the pressure within the chamber to or towards atmospheric pressure. Because of the time for which the valve is open or the rate at which air can enter through the valve, the chamber may not be returned completely to atmospheric pressure between the pulses of pressure and a small amount of negative pressure may remain each time in the chamber at the end of the pulse. This might be, say, between 0 and −20 mmHg (0 and −2.7 kPa) or more preferably between 0 and −10 mmHg (0 and −1.3 kPa), and more preferably still between 0 and −5 mmHg (0 and −0.67 kPa). Most preferably, the rate at which air can enter through the valve and the pulse period are such that the pressure within the chamber is returned to atmospheric pressure during each pressure pulse. In the most preferred embodiments, the change in the chamber pressure is substantially instantaneous such that the time taken to change the pressure takes only a small fraction of the time for which the valve is open, for example, less than 50%, preferably less than 25% and most preferably less than 10% of the time that the valve is open during a pressure pulse. It is preferred that the plot of pressure against time follows a substantially square toothed plot with sharp transitions at the pressure changes. In practice, some rounding of the transitions may occur. Similarly, the pressure source should have sufficient capacity to bring the pressure to the desired negative or positive pressure as quickly as possible and preferably within similar working levels as that for the valve.

For certain applications, it may be preferred to vary the pressure between atmospheric pressure, or substantially atmospheric pressure, and a positive pressure of corresponding magnitude to those values given above for negative pressure. In other applications, oscillating the pressure between positive and negative pressures may be beneficial. For example the pressure may be pulsed between −40 mmHg (−5.3 kPa) and +15 mmHg (+2 kPa) with time sequences of 7 seconds drop in pressure to −40 mmHg (−5.3 kPa), 7 seconds rise in pressure up to 0 mmHg (0 kPa) and continuation of increased pressure through to +15 mmHg (+2 kPa) over the next 5 seconds followed by a drop to 0 mmHg (0 kPa) over the following 2 seconds with the sequence repeated and the pressure dropping to −40 mmHg (−5.3 kPa) over the next 7 seconds.

In a number of earlier known systems in which an oscillating pressure was applied to a patient, it was thought best to vary pressure in time with the heart beat. The present inventors have found that a longer period to the oscillation is better. That is to say that each step of negative pressure application should last more than one second, preferably more than three seconds, more preferably five seconds or longer, most preferably about seven seconds or longer. However there is an optimum since longer pulses greater than 30 seconds and constant pressures tend to reduce blood flow. Relaxation of the pressure to atmospheric pressure should be for corresponding periods, although may be of slightly different duration.

Preferably the times for which the valve is open and shut are not equal, and hence the pulses of negative/positive pressure and atmospheric pressure are not equal. Preferably the length of the negative/positive pressure pulse is longer than the period "at rest" when the pressure is at atmospheric pressure or returning to atmospheric pressure.

Preferably it is 5% longer or greater, more preferably greater than 10% longer and most preferably more than 25% longer. In one embodiment that has been found to work particularly well, negative pressure was built up for 7 seconds and released for 10 seconds.

The valve could be positioned in the communication path to the pressure source, but is preferably provided in the chamber housing, and positioned near the top of the chamber when it is in use so that air is bled into the air pocket rather than the liquid. Under negative pressure conditions, if the valve were positioned below the level of the liquid, it would create bubbles in the liquid and may affect the temperature of the liquid. Under positive pressure conditions, submerging the valve could result in liquid being ejected from the chamber. A microprocessor can be programmed to operate the valve and different settings could be stored for different applications.

The housing could be any shape, for example, rectangular, i.e., box-shaped, but is preferably tubular and of circular or oval cross-section, i.e., generally cylindrical. A rounded surface is more able to withstand negative pressures and allows the housing to be rocked slightly from side to side to alleviate discomfort to the patient. The seal may restrict movement of the limb with respect to the chamber so small amounts of rotation of the limb can be taken up through rolling the housing slightly. This would not be possible with a housing of triangular or square cross section having flat sides, where a more flexible sealing system or rocking surfaces may be required in certain cases. If the device is intended specifically for the lower leg and foot of a patient, then it may comprise two sections; one tubular section to house the patient's leg and a box section at the end that is of larger dimension to accommodate the patient's foot. The tubular section may allow the device to be rocked from side to side whilst the flat-sided box section hangs off to one side of the operating table. The important advantage is that the shape of the chamber is not critical to the operation of the device, other than it must be of a size sufficient to accommodate the limb of the patient. As a result it can be made much more cheaply than existing devices yet benefits of improved thermal energy transfer to the patient can be achieved.

In embodiments where the housing comprises an elongate cylinder of circular cross-section having a curved side wall and a flat end wail, preferably the connection to the pressure source is provided in the curved side wail of the housing for positioning as a highest point in use. In this way, the likelihood of liquid being sucked out of the chamber by the negative pressure source is reduced. More preferably two connections are provided in the side wall of the housing, one proximate the end wall of the housing and other proximate the seal and opening at the other end of the housing. As it may be difficult to position a patient so that the limb is exactly horizontal, one end of the housing may be raised slightly higher than the other. Providing two connections in the housing that are connected to the pressure source by a common air line fitted with a Y-connector, ensures that at least one of the connectors is in communication with the pocket of air above the surface of the liquid. Preferably the Y-connector is positioned at a height above the surface of the liquid so that the liquid tends not to become drawn up one of the air lines if one of the connections becomes submerged, for example, when repositioning the limb of the patient. Under negative pressures of −40 mmHg (−5.3 kPa), a height of 50 mm or more is preferred for this. Alternatively, a valve could be positioned to select one or other or both of the connectors for connection to the pressure source.

The seal may be in any form which is capable of sealing the gap between the opening of the chamber and the portion of the limb, for example, a rubber cuff or the like. Under negative pressure condition, atmospheric pressure can assist the sealing engagement of the seal with the limb. Soft materials such as neoprene O-rings are preferred. A seal may be fitted around the limb prior to insertion in the chamber and then connected to the chamber to seal it off once the limb is positioned inside. One of the preferred uses of the device is for treating hypothermia where it is important to circulate the warmed blood from the peripheral region of the limb around the body and through to the core. Too tight a seal can act as a tourniquet and restrict this circulation. Where the device is to be used to apply positive pressures, additional means may be required to prevent escape of air. In one arrangement, the air line is fitted around the seal, so that increases in the positive pressure causes greater pressure to be applied to the seal in step when the chamber is at a higher internal pressure, In another embodiment an inflatable cuff, preferably of latex or the like, is used.

A preferred arrangement for alternating positive-negative pressures has been found where the seal, preferably made from rubber/silicone etc., is T-shaped and provided with two "wings" in the form of flaps that extend from a central sealing member into sealing engagement with the limb. One flap or "wing" extends inside the chamber and is pushed towards the skin surface by the positive pressure, whereas the flap or "wing" outside the chamber will be sucked towards the skin during the negative pressure period.

The seal is also important because it creates a region of relatively ischemic tissue in the skin beneath the seal during negative pressure. When the pressure is released vasoactive substances (potassium, ADP, adenosine etc.,) travel with the blood and dilates the arteries below to increase blood flow.

The liquid in the chamber is for transferring thermal energy to or from the limb. As mentioned above, preferably this liquid is water. For treating hypothermia, warm water at between 40 to 45° C., preferably 43° C. is used. Some patients will feel pain at temperatures greater than 43.5° C. For treating hyperthermia, cooler or cold water at temperatures of below 35° C., or more preferably 30° C. or below, is used. Water below 15° C. can cause the nerve "pain" fibres to start firing.

In situations wherein the temperature of the heat transfer medium or the amount of heat transfer surface available is not sufficient to effect a change in core body temperature fast enough, a regional anaesthetic may be administered to the limb, thereby blocking signals from thermoreceptors so as to decrease sympathetic activity to the vessels preventing vasoconstriction. By preventing shivering with a full surgical anaesthetic to the arm, say, with pethidin when trying to induce hypothermia, heat transfer from the body core can be improved. The combination of a regional anaesthesia with cooling, whilst being a preferred feature of the invention described above, is believed to be new in its own right.

Thus a second embodiment of the invention disclosed herein provides a system for effecting a change in the core body temperature of a patient comprising the simultaneous transfer of thermal energy from a limb whilst subjecting the limb to a pulsating pressure, preferably a pulsating negative pressure, wherein an anaesthetic agent is administered to the patient prior to the transfer of thermal energy to reduce sympathetic responses in the limb of the patient. The second embodiment can be used in conjunction with the apparatus for the other embodiments disclosed herein.

Thus in the above methods described with reference to the first embodiment of the invention, preferably the step of providing a regional anaesthesia to the limb, for example, by administering an anaesthetic agent to the patient, is included.

In a preferred arrangement, a regional anaesthesia is given in the brachial plexus prior to applying the method of the present invention to the arm of the patient. The regional anaesthetic has the following main effects:

Blocks sympathetic activity to the blood vessels, thereby dilating the vessels in the arm (efferent signals). This is important to the efficient operation of the method.

Blocks afferent nerve signals from all receptors in the arm to the central nervous system. They have effects on the temperature regulating centre reducing signals which tell the body to start heating/shivering/constriction.

Relieves the patient of pain, which again can be important for blood pressure control.

By anaesthetising the limb, e.g., the patient's arm, prior to its insertion in the devices described above, liquids at higher or lower temperatures than those suggested previously, i.e. greater than 43.5° C., more preferably greater than 45° C., or less than 30° C., more preferably 10° C. or below, could be used to provide a greater thermal energy transfer across the skin of the patient.

At temperatures less than 25° C., and preferably less than 23° C. where there is a temperature gradient of at least 14° C., regional anaesthesia is particularly beneficial because of the amount of control that this gives over the core body temperature of the patient, e.g., maintaining or lowering the core body temperature. Additionally, chilled fluids may be administered to the patient (e.g., at 4° C.) to lower the body temperature by a few (2-3) degrees, prior to maintaining the low core body temperature by operating the device at 23° C. Both the induction of hypothermia (e.g., for stroke treatment) and treating hyperthermia could be done this way.

This second embodiment of the present invention also has application with some of the prior art devices and may provide a solution to the poor heat transfer rates that are currently achievable with those devices.

Additionally, situations may occur wherein wrinkling of the skin is caused by long exposure of the skin to liquid when the limb is placed in a device of the present invention. However substances may be added to the liquid to minimize this and alleviate any discomfort caused. For example softeners and moisturizers know in the art may be added to the liquid to reduce the wrinkling of the skin. Another solution is to use a water perfused mat that is arranged to provide simultaneously pulses of pressure to the limb where it is in contact with the mat whilst transferring thermal energy. These systems are known from the prior art. However, an ordinary heating blanket (water perfused) will have too much air and areas of non-contact to be effective enough to regulate body temperature reliably.

A solution to this problem is to utilise "double" suction, in which the negative pressure is divided into an "internal" and an "external" negative pressure. The internal pressure, being only a few mmHg, e.g., less <−5 mmHg (<−0.67 kPa), is applied between the skin and the water-perfused part of the device (e.g. a blanket). This will suck the material towards the skin, and maximize the contact between the water compartment and the skin. The internal pressure may be constant, pulsed or administered only at initial administration of the pressure to ensure adequate contact of the mat or water blanket to the limb, thereby optimising the heat transfer effect. Thin material, elastic or non-elastic with relatively high thermal conductance, for example, silicon, latex etc. Then the external pulsating pressure (e.g., pulses of negative pressure) is applied outside the water blanket. This double pressure is believed to be critical to optimise the heat transfer effect. Thus this system would provide a way of transferring thermal energy to or from a subject, whilst simultaneously providing a pulsating pressure, in applications where direct contact with water is not wanted. The device could take the form of that used in the first embodiment of the invention except that instead of the limb being immersed in a liquid contained within the chamber, the limb is instead surrounded by liquid contained within the chamber but separated from that liquid by a layer of flexible material.

Thus, in a third embodiment of the invention disclosed herein, there is provided a device for applying a pulsating pressure to an area of skin on a limb of a body comprising a pressure chamber into which the limb can be inserted, a barrier layer of flexible material housed within that chamber for engagement against the skin, the barrier layer defining an inner region within the pressure chamber for receiving the limb which is separated from a flow of liquid within the chamber, wherein the device includes an element or means for generating a pulsating pressure within the pressure chamber, and an element or means for generating a negative pressure between the barrier layer and the area of skin to maintain the barrier layer in contact with the area of skin. Preferably the barrier layer takes the form of a sleeve extending along the middle of the device, e.g., along a central axis of a cylindrical pressure chamber. This ensures contact over a greater surface area of the limb than prior art devices which may contact less than 50% of the limb, e.g., by contacting just one side of an arm. The flow of liquid may be partially contained by the walls of the pressure chamber acting as a containment vessel or contained within a water perfused mat.

With this embodiment, the most important feature is to keep the region between the skin and the water barrier layer substantially free from air (vacuum). This helps to ensure that the thin material containing the water will stick on to the skin even if there is an external pulsating pressure being applied. The "vacuum" in this region (e.g., 1-3 mmHg) may be constant instead of pulsating together with the external pressure. Sweat from the skin of the patient will accumulate in this region between the skin and the barrier layer which will assist in the heat conduction.

This invention also provides a method of applying a pulsating pressure to an area of skin on a limb of a body using the above described apparatus for the benefits described in relation to the other inventions. The method includes the steps of generating a negative pressure between the barrier layer and the area of skin, generating a flow of liquid within the pressure chamber adjacent the skin, generating pulses of pressure within the chamber, preferably pulses of negative pressure, and transmitting the pulses of pressure to the skin through the barrier layer. Preferably the method includes transferring heat to or from the skin whilst simultaneously applying pressure pulses. Thus surrounding the limb with a heat transfer medium, either by immersing it in the medium or separating it from the medium by a thin flexible membrane which is drawn tight onto the skin via suction, provides a common advantage of maximising the heat transfer area available, making the apparatus more effective at influencing the core body temperature. Furthermore, the reduction or prevention of a response in the sympathetic nervous system, at least locally in the limb through an anaesthetic agent, provides the advantage of maximising the heat transfer across the area available, again making the apparatus more effective at influencing the core body temperature.

Other possibilities for the device are also envisaged. For example, the device could have walls containing salts that, after being catalysed, can produce heat by an exothermic reaction. This could be of benefit in an acute situation where it is necessary to start heating quickly and perhaps where an external power source is not available. This heating means may be in addition to the other heating sources, for example, to be used as an emergency heat source.

Another possibility for emergency equipment is to have the entire device made of a lightweight inflatable material. Using a high pressure source, the device can be inflated so that the walls become stiff. The high pressure source (for example, a pressurised gas) can then be used to power the pulsating pressure for a period until external power can be provided from elsewhere.

One further possibility is to provide different pressures and/or temperatures in different compartments within the device so that, for example, the patients' hand can be kept warm to make the blood follow the superficial veins when it returns to the core, but on its way back the blood can then be cooled because it is more accessible. It is seen that this could improve core cooling rates.

Certain preferred embodiments will now be described by way of example and with reference to the accompanying drawings, FIGS. 1-13.

FIG. 1 illustrates a system for applying a pulsating pressure to a local region of the body. Shown fitted to the arm 1 of a patient 2 is a device 3 comprising a pressure chamber 4 having an opening 5 at one end into which the arm 1 is inserted. A seal 6, fitted to the arm 1, seals the pressure chamber 4 from external conditions. The pressure chamber 4 is provided with an inlet 7 and an outlet 8 for feeding a liquid 9, for example, warm water, into and out of the pressure chamber 4. Connectors 10, 11 may be fitted to the inlet 7 and outlet 8 respectively to connect easily the flow of liquid. Valves (not shown) can be used in these positions to control the flow of liquid. As shown in FIG. 1, the arm 1 is immersed in the liquid 9 but an air gap 12 exists above the liquid 9. In one embodiment the pressure chamber 4 is only three quarters filed with liquid 9. The pressure in this air gap is pulsated to generate pulses of. pressure that are transmitted to the arm 1 of the patient 2 via the liquid 9.

In the illustrated embodiment, the pressure chamber 4 is cylindrical in shape and a region of the circumferential wall 13 is provided with a connection piece 14 in communication with a pressure source 15. Preferably two connection pieces 14 are used with connectors 16. Valves may be provided to isolate the connection pieces 14 as desired (for example, in place of connectors 16). The pressure source 15 is preferably a suction device to suck air out of the pressure chamber 4, i.e. to create a negative pressure in the pressure chamber 4.

In order to pulsate the pressure, air is bled back into the pressure chamber 4 from outside. An air inlet at connection 17 with a controlling valve 18 can be provided to bleed air back into the air gap 12. Alternatively, and more preferably, air can be introduced into the pressure lines 19 linking the pressure source 15 to the device 3 through connection 14, for example, via a regulator 20. For both arrangements, connection 17 can also provide an inlet for filling the pressure chamber 4 with water prior to starting the pump. A pressure recorder 21 with an output 22 is provided to monitor the pressure within the device 3. The regulator 20 (for example comprising magnetic valves) and any additional valves provided can be controlled with a suitably programmed computer 23.

Figure 2A:
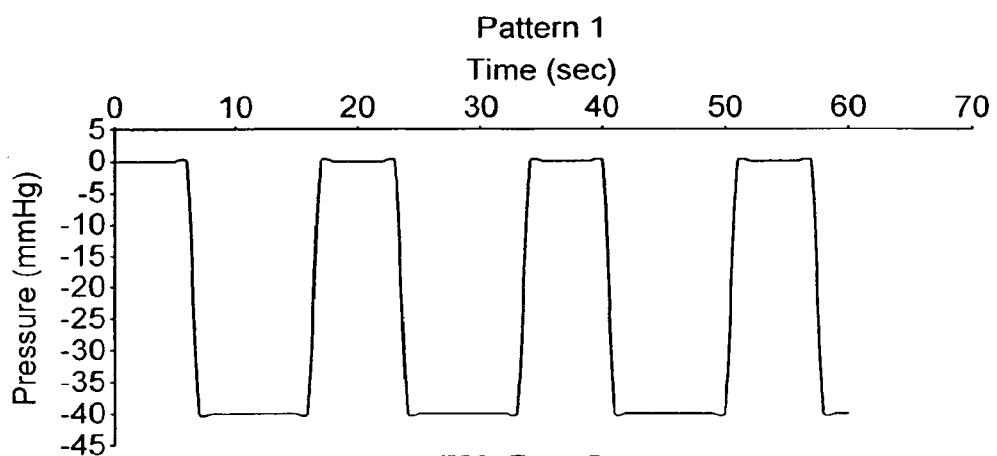
FIGS. 2a to 2e illustrate various pressure curves that might be used according to the state of the body.
Figure 2B:
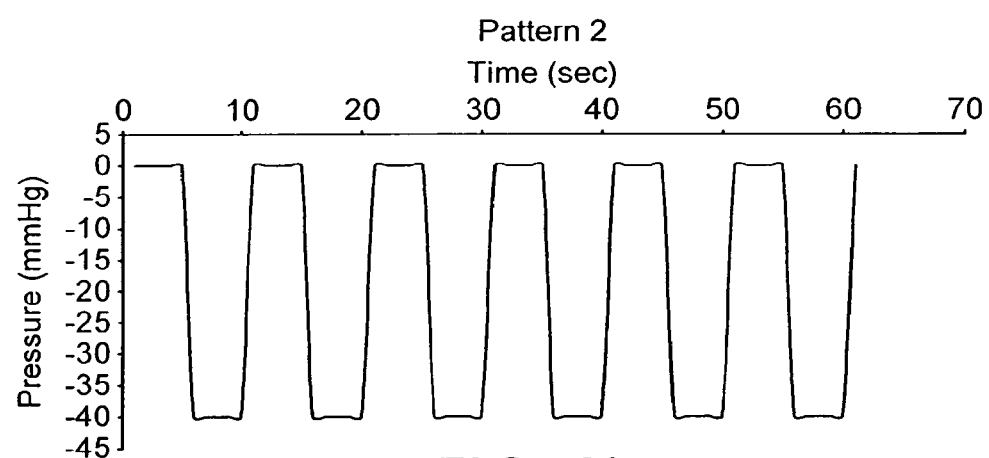
Figure 2C:
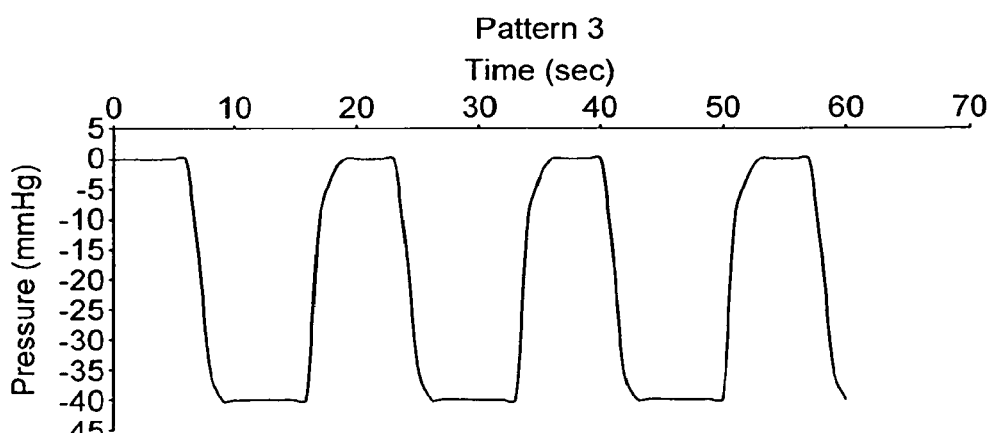
Figure 2D:
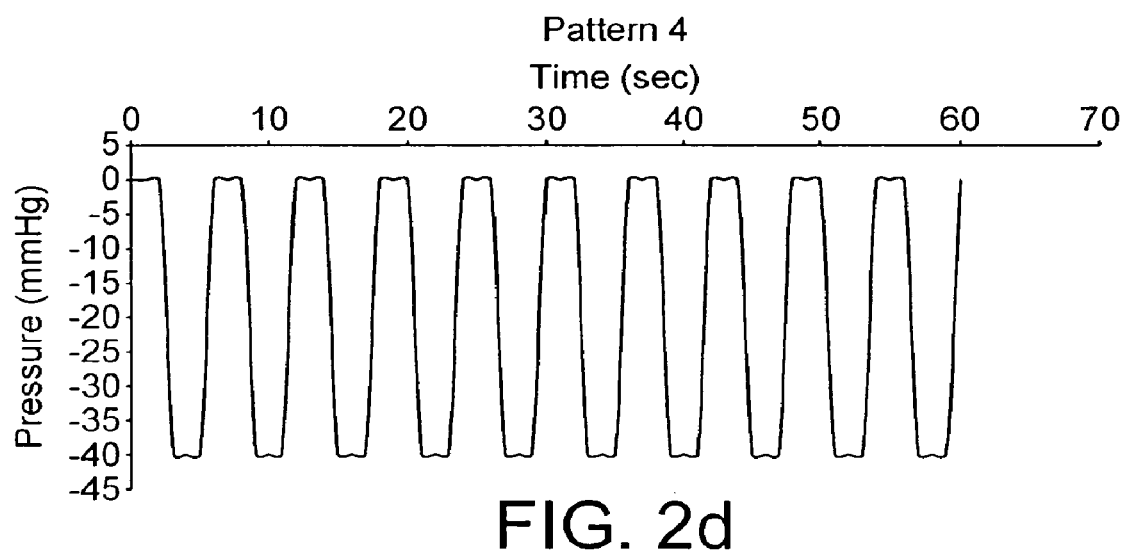
Figure 2E:
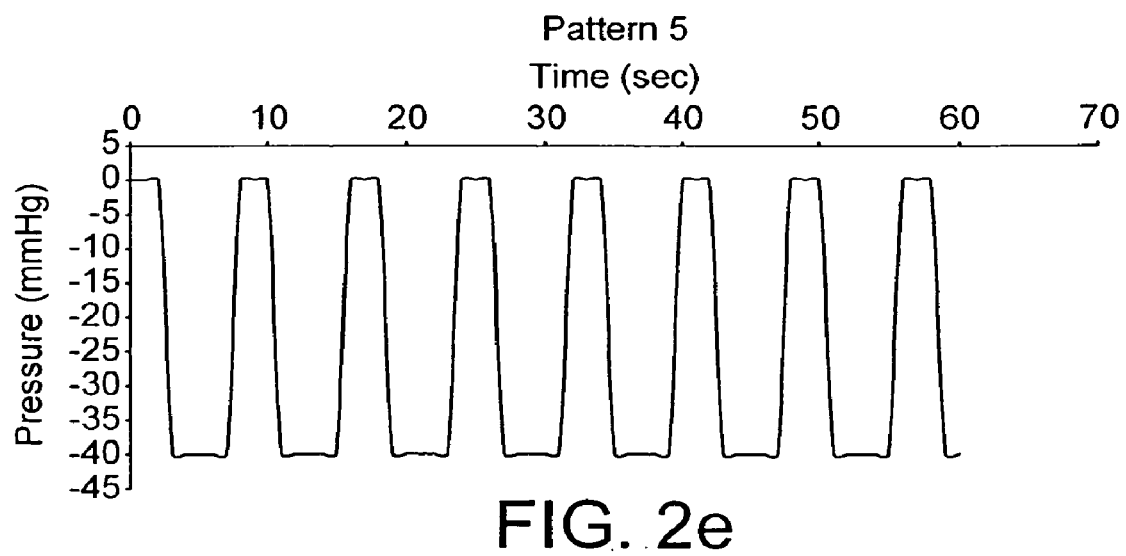

FIGS. 2a to 2e illustrate five examples of pressure curves that could be generated within the device 3, according to the state of the body and the condition being treated. In FIG. 2a, pressure varies between 0 and −40 mmHg (0 and −5.3 kPa) for periods of 7 and 10 seconds respectively. In FIG. 2b, the pulses last 5 seconds in a complete cycle time of about 10 seconds. In FIG. 2c the pulses are about 7 seconds in length. In FIG. 2d, the pressure is oscillated between 0 and −40 mmHg (0 and −5.3 kPa) for pulses of about 3 seconds each. In FIG. 2e, the negative pressure pulse lasts about twice as long as the time at atmospheric pressure.

Figure 3:
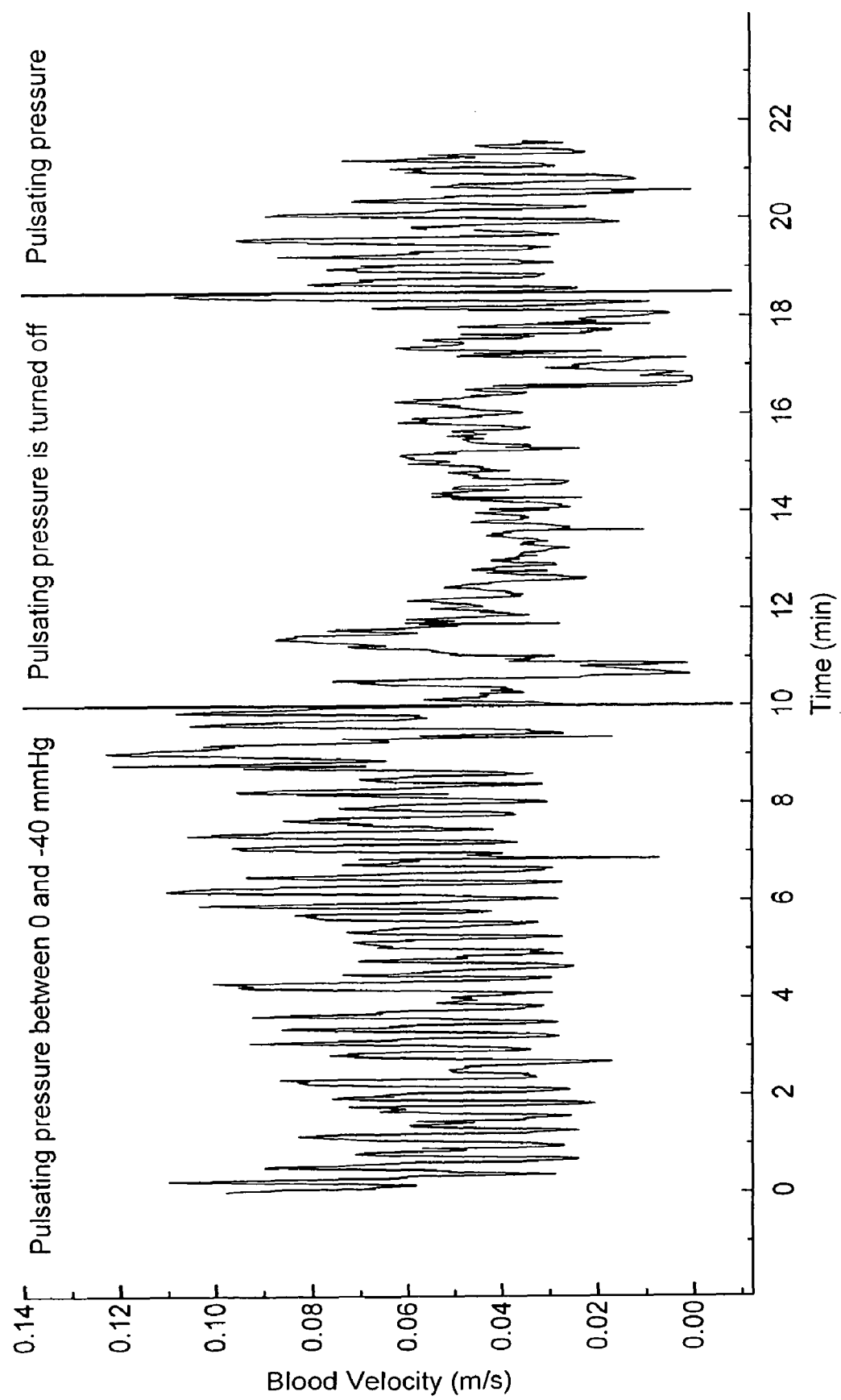
FIG. 3 shows a plot of blood velocity in the brachial artery against time illustrating the change in blood velocity as the pulsating pressure is switched on and off.

In FIG. 3, blood velocity (in essence, blood flow) in the brachial artery is shown with respect to time and how this varies under the influence of pulsating negative pressure and when the pulsating pressure is switched off. Blood velocity/ flow was measured using ultrasound Doppler and laser Doppler measuring techniques. Ultrasound Doppler, which measures blood velocity, is an important technique as measurements are made outside the device. Making the reasonable assumption that the blood vessel diameter is constant, then the velocity will be proportional to flow (volume/time). The values were transferred to a computer by an ECG recording, the velocities can be sampled beat by beat. As shown in FIG. 3, the pulsating pressure leads to a significant increase in the mean measured arterial blood velocity/flow.

Figure 4:
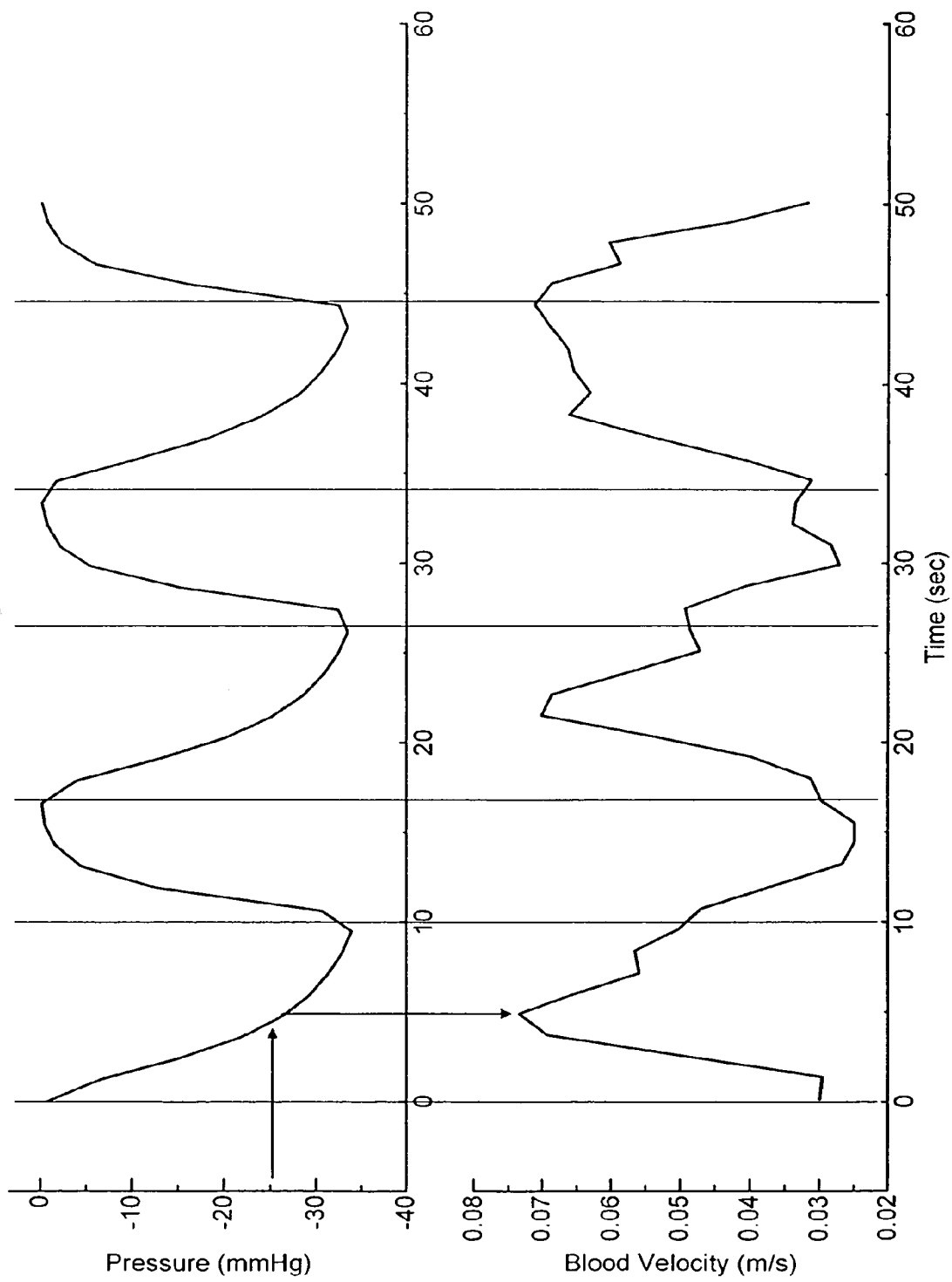
FIG. 4 illustrates the effect pulses of pressure have on blood velocity for pulses that are approximately 10 seconds (negative pressure) followed by releasing and 7 seconds without pressure (normalizing)

FIG. 4 shows a detailed one minute recording. The negative pressure is built up for 10 seconds and released for 7 seconds (upper panel). The blood velocity in the brachial artery is measured outside the pressure chamber 4. The blood velocity increases to a certain point, about −25 mmHg (−3.4 kPa), before it drops. This is thought to be due to a reflex constriction of the arteries because of the venus pooling. Letting the pressure drop again, facilitates the immediate and repeated increase of blood velocity without the reflex restricting the blood flow as can happen with a constant negative pressure.

Figure 5:
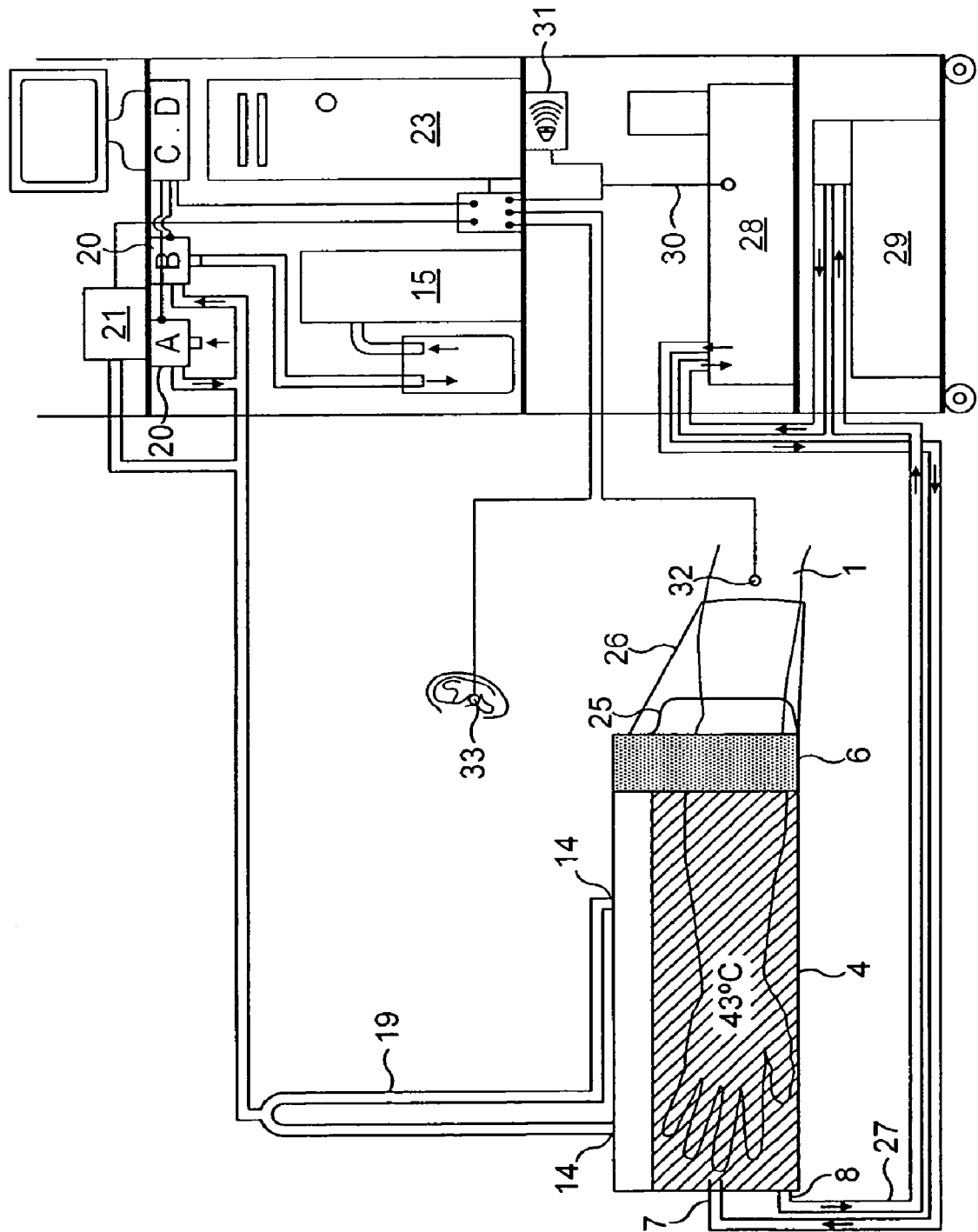
FIG. 5 illustrates a preferred embodiment of the apparatus in more detail.

FIG. 5 illustrates another embodiment of the apparatus. The same reference numerals as used in FIG. 1 have been used in this embodiment where they correspond. The pressure chamber 4 comprises an acrylic tube. In a preferred embodiment, the tube had a diameter of 16 cm and a length of 50 cm. The seal 6 comprises a ring of carved POM 24 (diameter 16 cm×10 cm) as an extension piece supporting an inner neoprene seal 25 and an outer rubber seal 26. Inlet 7 and outlet 8 are provided to feed liquid, for example, water, via feed lines 27. These connect to a water bath 28 for controlling the temperature of the liquid and to a pump 29, for example, a peristaltic pump for circulating the liquid.

The feed lines 27 are preferably silicone except for where they extend through the water bath. In the water bath 28, copper pipes are used to ensure good heat transfer. The copper pipes are preferably about 6 m long, ensuring equilibrium of the water temperature between the water bath and the water in the pipes. The water bath could heat the water to 45° C. and cool it to 4° C. Higher or lower working temperatures may be preferred as desired. Insulating material can be used to maintain operating temperatures. The water bath 28 may include a thermometer 30 and an alarm 31 to warn of dangerous operating temperatures.

Preferably a peristaltic pump 29 is used to circulate the liquid and preferably it is positioned at a lower level than the pressure chamber 4, thus letting gravitational forces, and the suction created by the pump, feed the pump. Because of this position of the pump 29, the amount of water going into the pressure chamber 4 always matches the volume of water coming into the pump 29, preventing pooling of water in the pressure chamber 4. By comparison, other pumps seemed to need a rather advance regulating system to match input/output.

Temperature sensors 32, 33 can record the skin temperature and tympanic temperature in the ear of the patient 1.

To generate negative pressure within the pressure chamber 4, valve B of the regulator 20 is open, connecting the interior of the pressure chamber 4 with the suction device 15. After a period of time, preferably 10 seconds, valve B closes and valve A opens. Valve A bleeds air into the pressure chamber 4, returning it to atmospheric pressure. The valve A remains open for a further period of time, preferably seconds. Valve A is then closed and valve B opened to repeat the cycle.

Figure 6A:
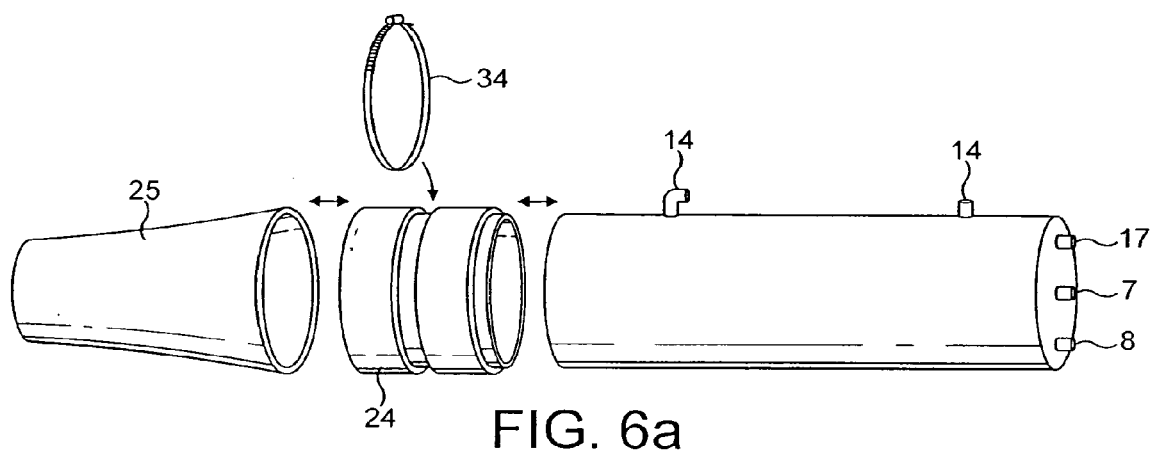
FIGS. 6a-6d illustrate further aspects in detail of the pressure application device used in the apparatus of FIG. 5.
Figure 6B:
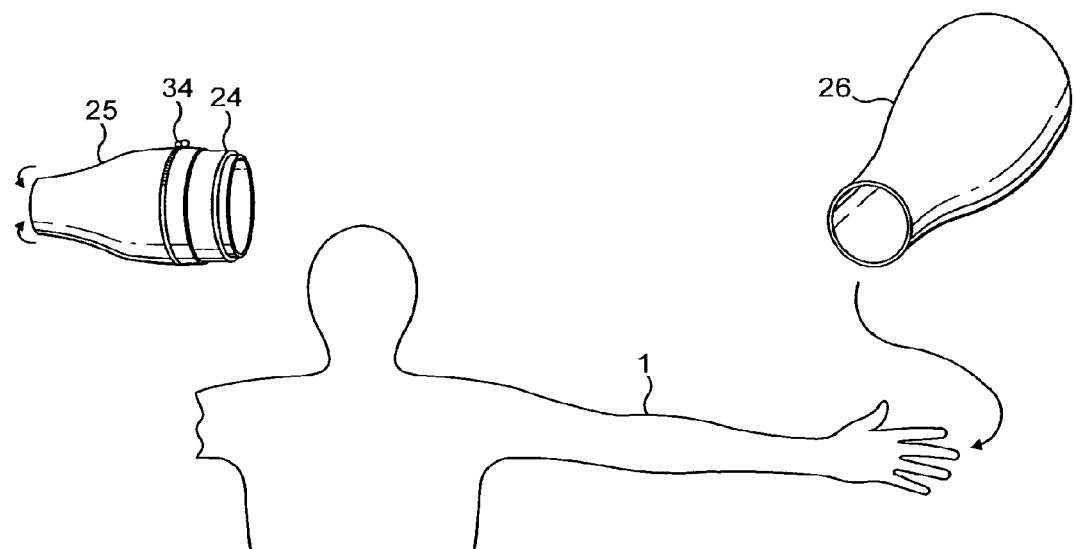
Figure 6C:
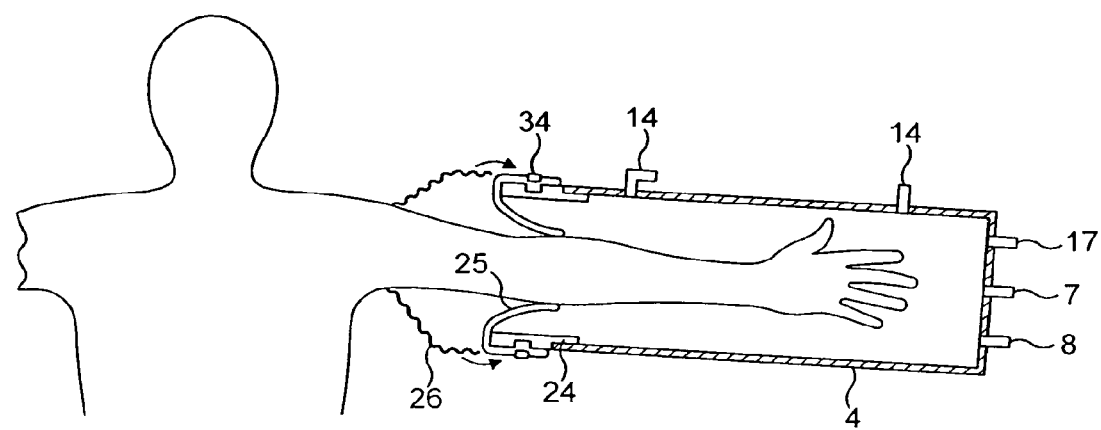
Figure 6D:
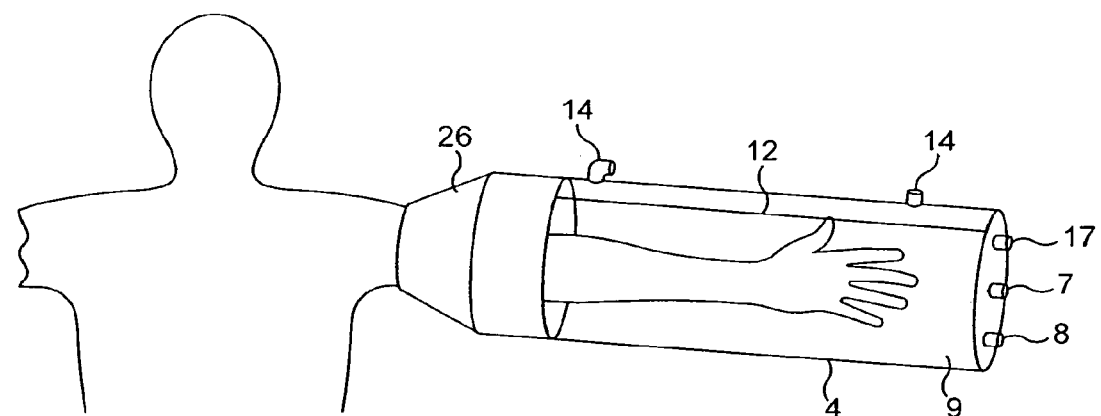

FIG. 6a shows an exploded view of the pressure application device 3 used in FIG. 5. A jubilee clip 34 retains the neoprene seal 25 on the carved POM extension piece 24.

To fit the pressure chamber 4 to the patient's arm 1, first the rubber seal 26, which is in the form of a tapered hose, is slid up the arm. Then the neoprene seal 25 with the extension piece 24 is slid onto the arm below the rubber seal 26. The arm 1 is then inserted into the pressure chamber and the extension piece 24 is attached to seal off the pressure chamber. The rubber seal 26 is rolled down over the neoprene seal 25, extension piece 24 and top of the pressure chamber 4 to ensure proper sealing. The pressure chamber 4 is then circulated with warm or cold water and pulses of pressure are generated within the pressure chamber 4.

Figure 7A:
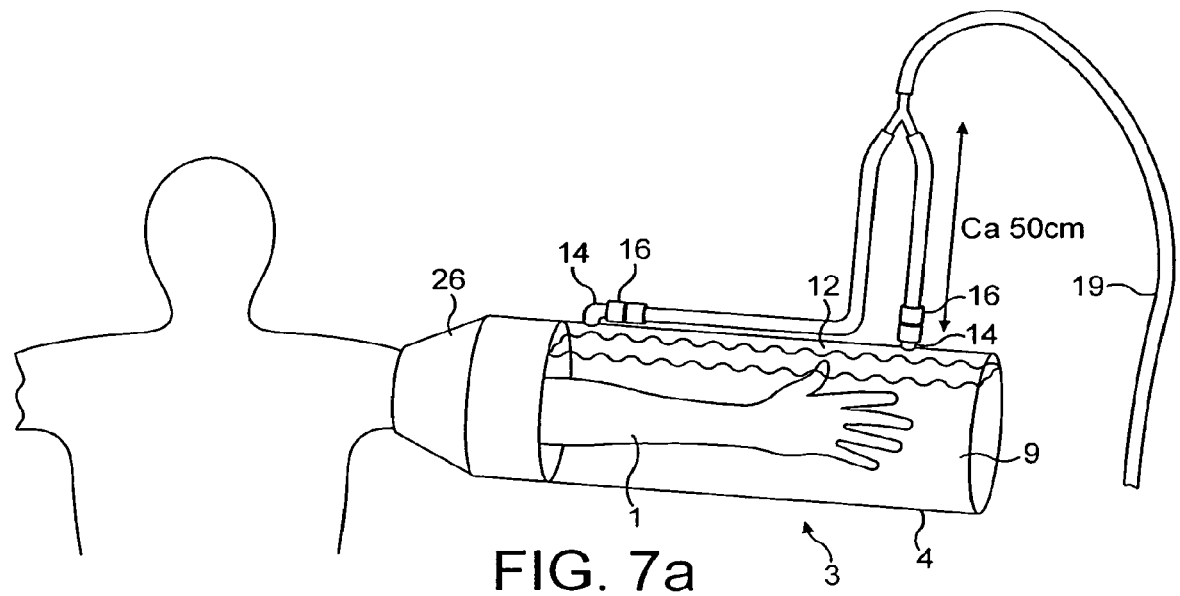
FIGS. 7a-7c show how the pressure application device is able to operate at different angles.
Figure 7B:
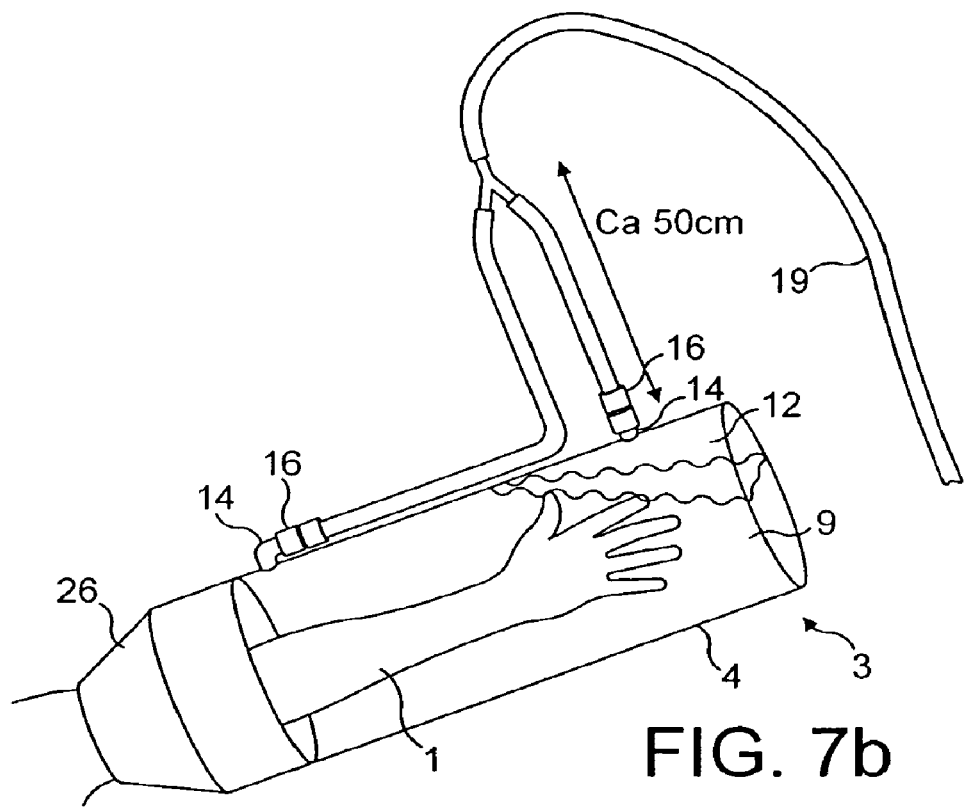
Figure 7C:
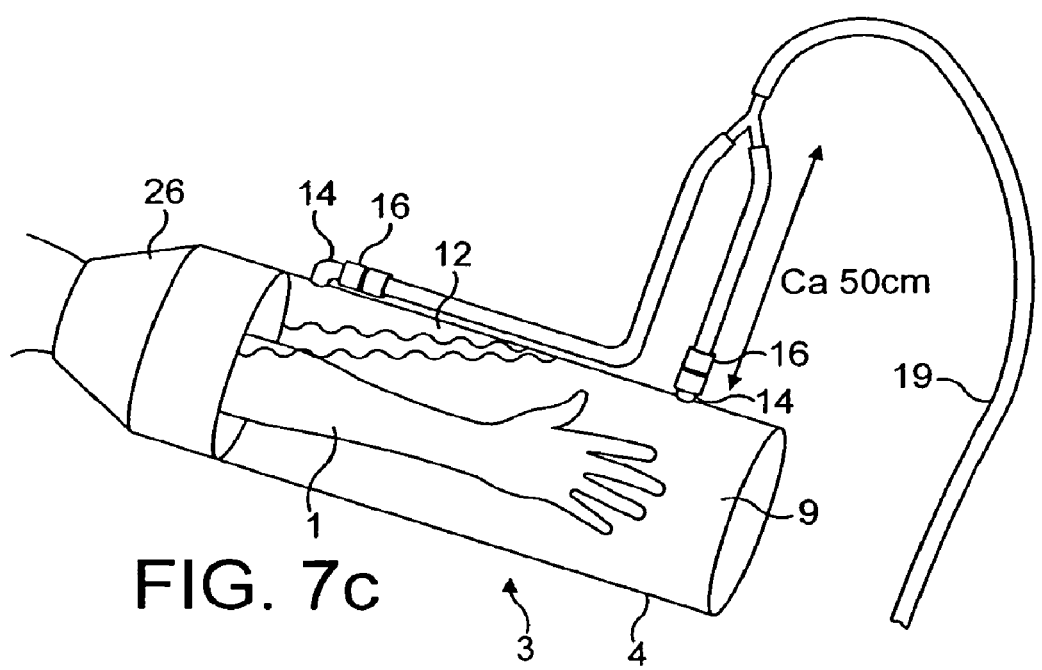

FIGS. 7a to 7c show the pressure application device 3 operating at different angles. The provision of two connection pieces 14 connected to pressure lines 19 ensures that at least one of the connection pieces 14 is located in the air gap 12. This is important as the patient 1 may be in a declined or inclined position to assist an operation.

Figure 8A:
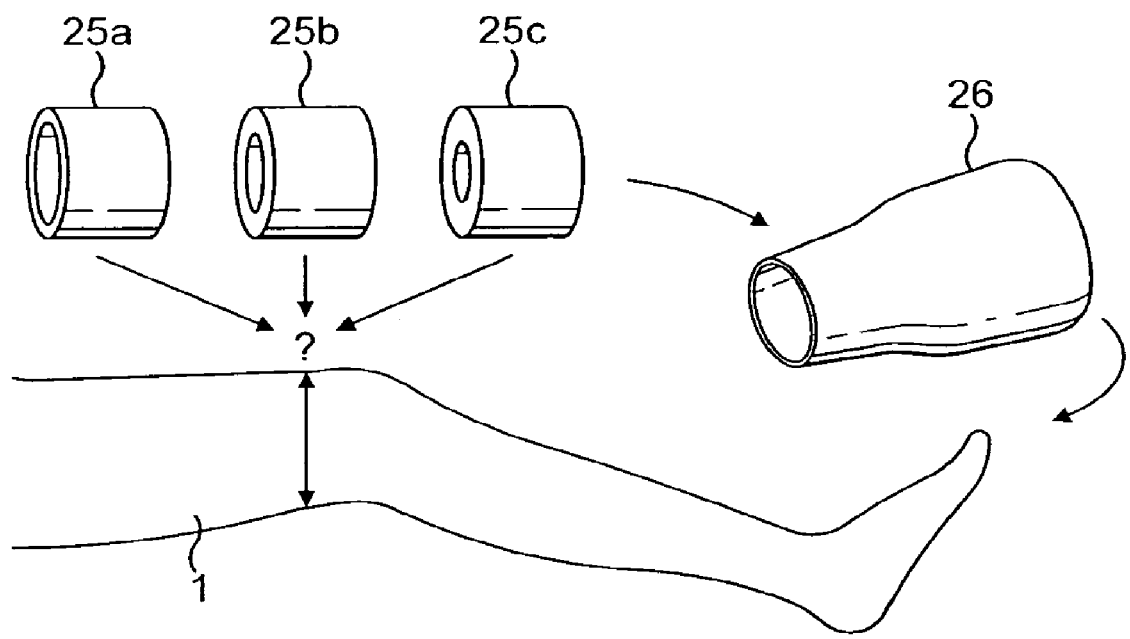
FIGS. 8a-8d show a preferred pressure application device for use on a lower leg and foot being fitted to a patient.
Figure 8B:
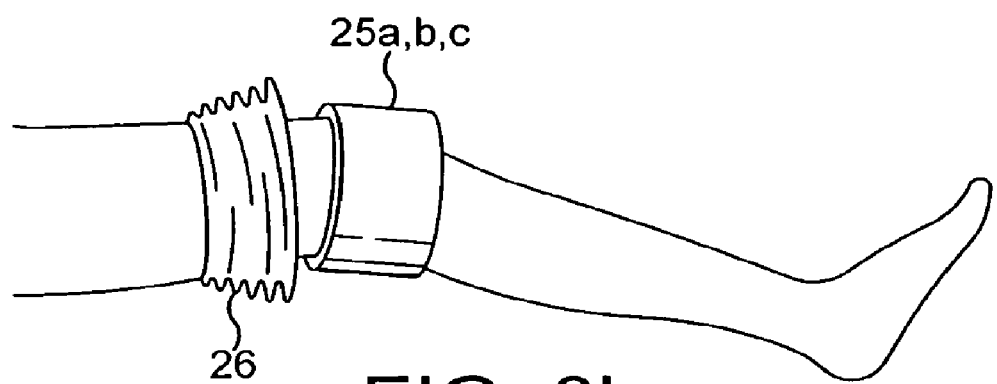
Figure 8C:
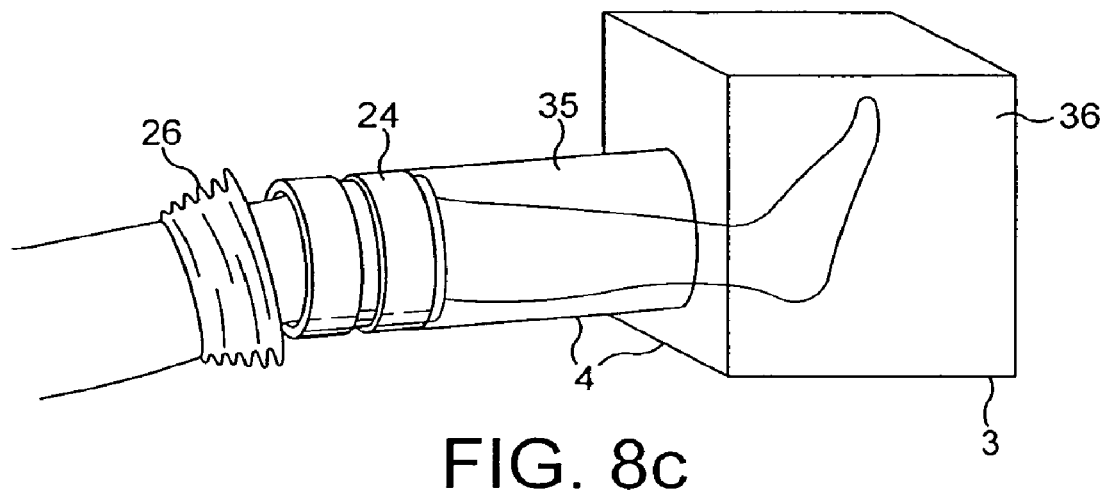
Figure 8D:
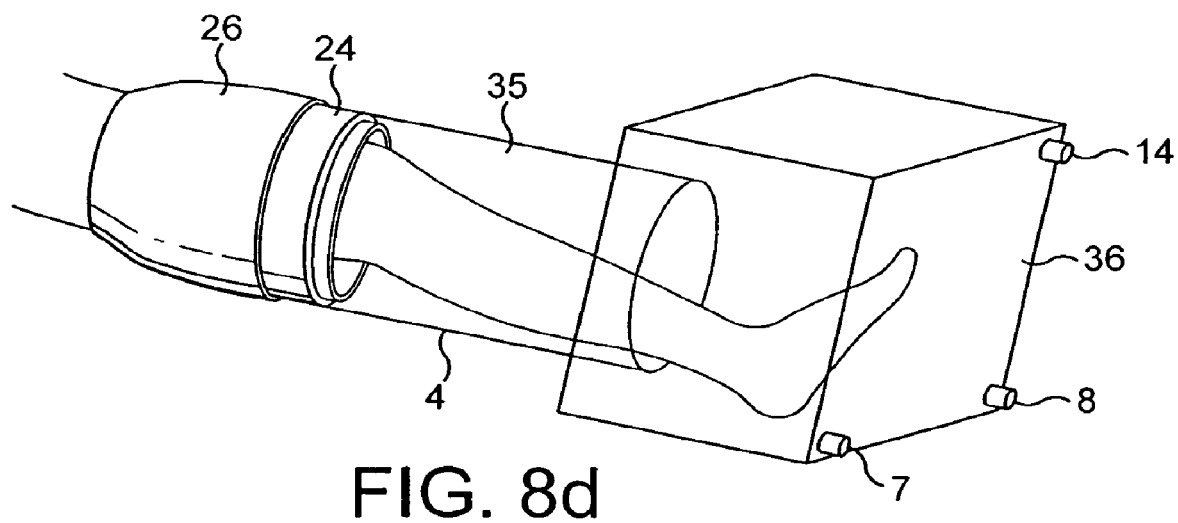
Figure 11:
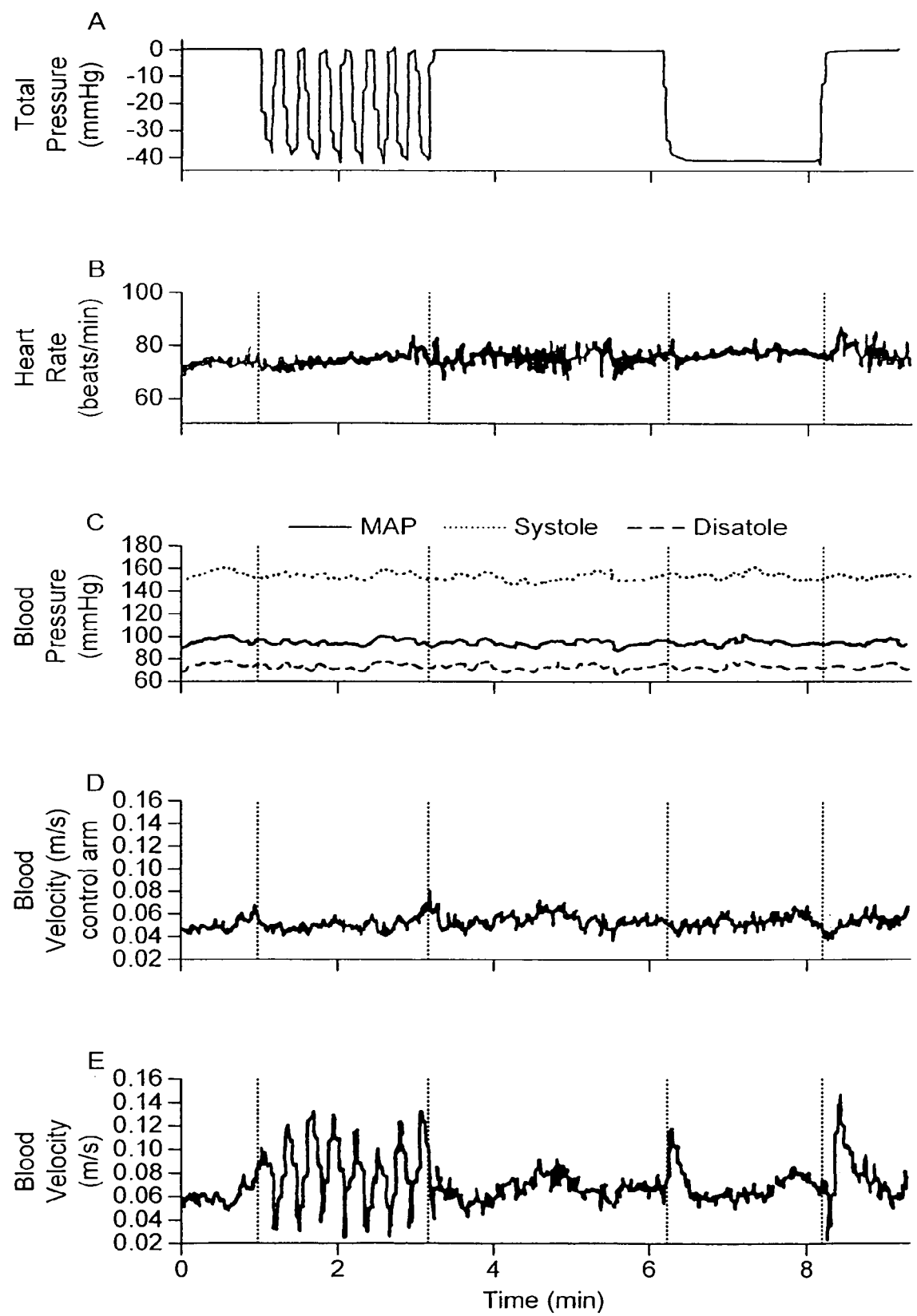
FIG. 11 shows a comparison of the blood velocities of an arm subjected to pulsating pressure and a control arm.

FIGS. 8a to 8d show a pressure application device 3 that is adapted for use on a leg. Depending on the width of the knee, the most appropriate size neoprene seal 25a, 25b, 25c is chosen and fitted to the patient. The rubber seal 26 would then fit over one end of the extension piece 24. As seen in FIG. 8c, the pressure chamber 4 comprises a cylindrical section 35 for the patient's leg and a box section 36 for the foot. The cylindrical section 35 would allow the device 3 to be rolled from side to side slightly to alleviate discomfort in the patient. In this embodiment, a single connection piece 14 is provided for communication with the pressure source 15. An inlet 7 and outlet 8 are provided at the base of the box section 36 for circulating water within the device 3.

FIG. 9 illustrates a further device 3 having a sleeve 37 of a flexible material such as a latex membrane to provide a barrier between the circulating water and the skin of the patient. Such a device might be used to avoid wrinkling of the skin. The sleeve 37 divides the pressure chamber 4 into two compartments; an inner compartment for receiving the limb and an outer compartment for the circulated liquid. A connection 38 is provided in communication with the inner compartment to create a small negative pressure of preferably 0.5-1.0 mmHg of negative pressure (−0.065 to −0.13 kPa). This sucks the sleeve 37 into full contact with the limb to ensure good thermal energy transfer. Pressure pulses are applied to the circulating water through the connection to the outer compartment via pressure lines 19 in the normal way. The pressure in the outer compartment can be reduced accordingly, but this is probably not necessary. Leaks are less likely and cleaning of the system is easier.

A similar flexible sleeve incorporating a heating element may also be used as a way of providing thermal energy to the patient (not shown). For such an arrangement an electric cable would need to be provided of a sufficient length to allow the sleeve to be fitted to the patient prior to the patient inserting his arm into the pressure chamber 4. Alternatively some form of induction heating may be possible.

FIG. 10 illustrates the results of a comparison between the device of the present invention and a known system of forced air warming which is marketed under the registered trade mark of "Bair Hugger"®. Bair Hugger® is made of blankets which cover whatever part of the body is not being used in an operation. In abdominal surgery this can be a problem because the larger parts of the body, e.g., head, neck, abdomen and legs cannot be warmed by the force air warmer because access is required for other operations. Abdominal surgery is also often long lasting e.g. more than two hours and patients developing hypothermia is a huge problem. Hypothermia can cause severe problems for patients including cardiac arrhythmia and increased risk of infection and ischemic heart disease. In the study a pressure application device as shown in FIG. 1 was applied to the patient's arm and this was found to be enough to keep the patient warm.

In one additional test trial, a plexus anaesthesia was administered in the left arm to block signals from thermoreceptors to the central nervous system and thereby to decrease sympathetic activity to the vessels, preventing vasoconstriction. After inducing regional anaesthesia the pressure within the chamber was pulsated and 10° C. water was circulated in the pressure chamber to induce hypothermia. The pressure inside the chamber was pulsated between 0 and −40 mmHg (0 and −5.3 kPa). The core temperature decreased from 36.9° C. to 36.3° C. To induce anaesthesia the doctor used 40 ml 0.1% Xylocaln. This did not give a full regional anaesthesia of the arm and the subject started to shiver a little bit during the last part of the cooling. Full surgical anaesthesia of the arm would be possible with pethidin so as to prevent shivering. It is believed that if the same procedure were used on patients in general anaesthesia it would probably have been even easier to induce hypothermia.

Measurement of blood flow was done using ultrasound Doppler and laser Doppler. In the preferred examples, the ultrasound Doppler technique was used to Measure blood velocity (m/sec). If there is no change in vessel diameter, the velocity is proportional to flow (volume/time). Laser Doppler was also used to record blood flow (a.u.) in the skin. The registrations were transferred to a computer by an A/D-card and sampled at 50 Hz. Using a simultaneous ECG recording, the velocities were sampled beat by beat. In another trial, computer was also used to open and close the valves, generating a pulsating pressure (10,11).

In an additional test trial, the effects of applying a local pulsating negative pressure on arterial blood velocities were studied. In the test trial subjects were comfortably positioned on a bed in a supine position, their right arm was abducted 70-90 degrees and positioned inside a custom built tube shaped transparent plexiglass chamber similar to the apparatus illustrated in FIG. 1. The chamber was sealed to the upper arm by a neoprene collar, which was attached to an adapter. An elastic rubber hose covered the adapter/neoprene collar and continued approximately 5 cm on the arm and about 5 cm distally on the tube. The chamber was connected to an adjustable medical suction device. A pair of computer-controlled magnetic valves was connected between the chamber and the suction device, making it possible to control the pressure inside the chamber. Each experiment for each individual subject was divided into 3 periods, each consisting of a 2-minute measurement period preceded and followed by 1 minute baseline recordings (See FIG. 11). During each period, the pressure inside the chamber was either 0 (=ambient pressure, −40, or pulsated between 0 and −40 mmHg. Pulsating pressure was applied to the right arm (experimental arm) and no pressure was applied to the left arm (control arm). The pressure applied to the right arm was pulsated in sequences of 10 seconds on and 7 seconds off. The order of periods in each experiment was randomized. Baseline recording started when the brachial arterial blood flow showed large fluctuations indicating that the subjects were in their thermoneutral zone.

Blood velocity was measured using ultrasonic Doppler and laser Doppler methods. The blood velocity of the right arm was measured from the right axillary artery and the velocity of the left arm was measured from the left brachial artery. A bi-directional ultrasound Doppler velocimeter (SD-100, GE Vingmed Ultrasound, Horton Norway) was operated in the pulsed mode with a handheld 10 MHz probe. The ultrasound beam was directed at an angle of approximately 45° to the vessel on the medial side of the arm, about 5 cm distal to the axillary fossa. As previously indicated, as a control, blood velocity measurements were also made in the left brachial artery. The SD-100 on the right hand side also had a built in three-lead surface electrocardiogram (ECG) which was attached to the right and left shoulder and to the lower edge of the ribcage in the left midclavicular line. Laser Doppler flux (LDF) was recorded from the pulpa of the second finger of the left arm (MBF3D; Moor Instruments, Devon, UK). In addition, instantaneous arterial blood pressure (BP) was obtained from the left third finger using a photoplethysmographic device (Ohmeda 2300 Finapres, Madison, Wis.). The chamber pressure was monitored with a digital manometer (Piezoresistive Transmitter Serie 23, Keller A G, Switzerland). The readings from the instruments were fed online to a personal computer and recorded at different frequencies. The same computer was preprogrammed to control the magnetic valves. The recordings were displayed realtime on a computer screen.

Instantaneous cross sectional mean velocities from the axillary and brachial arteries were calculated by the ultrasound Doppler Instruments, and together with the readings of LDF, BP and chamber pressure fed online to a computer for beat by beat time averaging, gated by ECG R waves. The analog signals were converted to a digital signal and recorded by the computer at 2 Hz and 50 Hz. The program calculated the heart rate (HR) based on the ECG signal.

FIGS. 11A-E show simultaneous recordings of chamber pressure, HR, BP and blood velocity in both arms from one subject. It shows blood velocity over time for the right (experimental) arm compared to the blood velocity over time for the left (control) arm. During the pulsating phase, the blood velocity in the right axillary artery shows large fluctuations, which are synchronous with fluctuations in pressure. At the onset and end of constant negative pressure there are large changes in blood velocity. There is a short increase in blood velocity, lasting about 15 seconds when the negative pressure is applied. At the withdraw of negative pressure there is a short lasting decrease in velocity. This is followed by another longer lasting, 15 second increase in velocity with another increase in pressure. The blood velocity in the control arm is at about the same value as baseline recordings in the opposite arm. There are no large changes in the velocities in the control arm. MAP and HR did not change during the experiment, a common finding to all experimental runs. Thus, pulsating negative pressure causes an increase in blood velocity compared to normal pressure.

Figure 12:
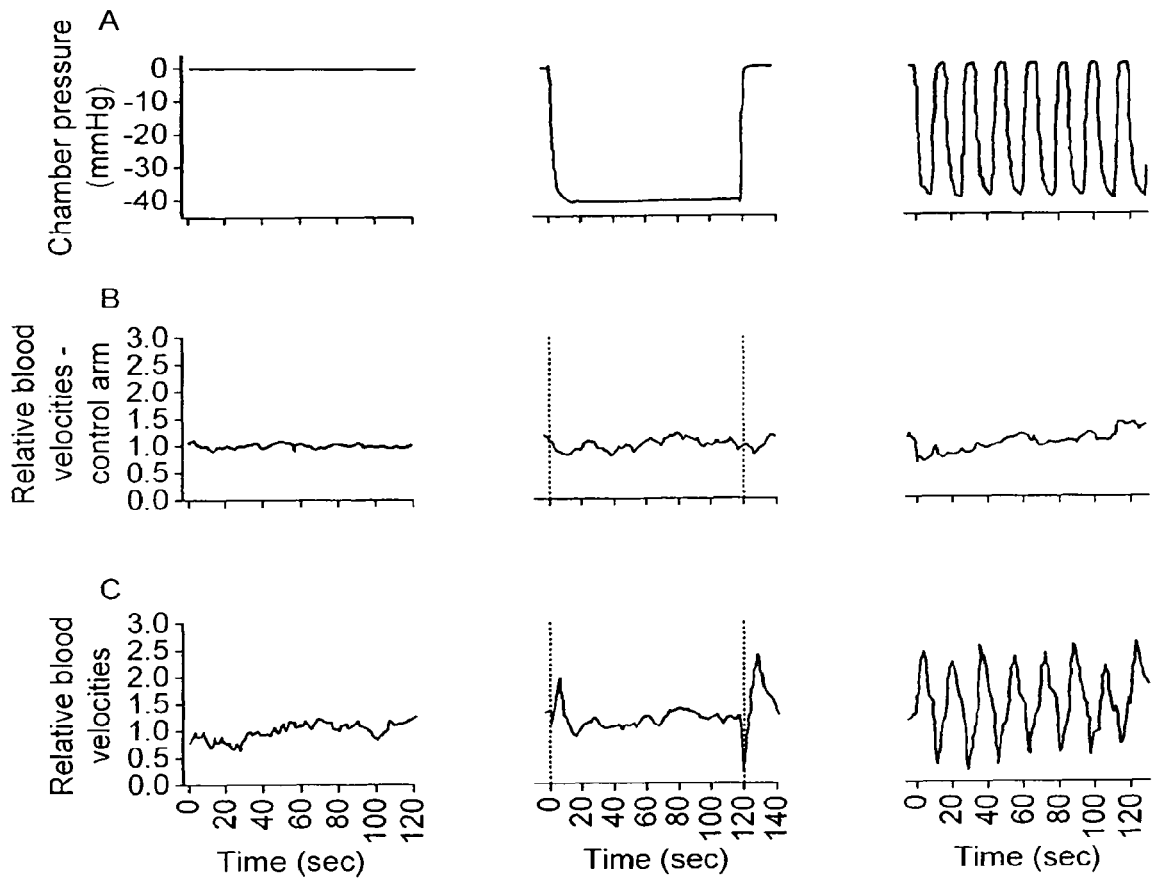
FIG. 12 shows a comparison of blood velocities of an arm subjected to normal, constant and pulsating pressure and a control arm.

FIG. 12 A-C shows chamber pressure compared to relative blood velocities from each the right (experimental) arm and the left (control) arm during normal pressure, constant negative pressure and pulsating negative pressure. The first column depicts normal pressure, the second column depicts constant negative pressure and the third column depicts pulsating negative pressure. The average blood velocity in the right (experimental) arm is 47.4% higher when pulsating negative pressure is applied compared to the average blood velocity under normal pressure. The average blood velocity is 16.9% higher when constant negative pressure is applied compared to the average blood velocity under normal pressure. The average blood velocity in the left (control) is approximately the same in each of these. Thus, pulsating negative pressure causes a much higher increase in blood velocity than constant negative pressure.

Figure 13:
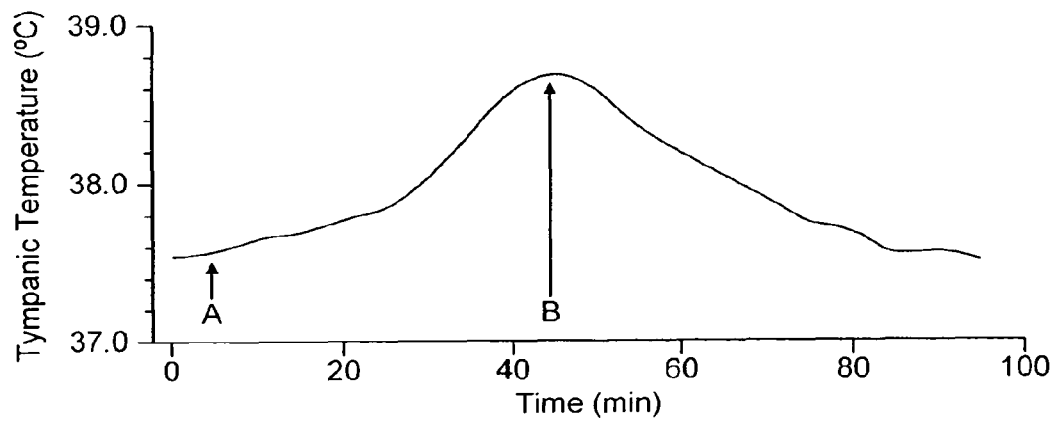
FIG. 13 shows the change in tympanic temperature of a patient over time during treatment for hyperthermia.

The present invention can also be used to cool down patients with hyperthermia. FIG. 13 shows the tympanic temperature of a patient with hyperthermia over time. A patient was exposed to 40-50° C. warm air and relative humidity of 40% for 1-2 hours and became hyperthermic with a tympanic temperature of 38.5° C. The body temperature was initially measured to 37.0° C. After the equipment was applied and registering on the computer started the temperature had risen to 37.5° C. At point A in FIG. 13, the tympanic temperature had risen to 38.7° C. and sweating had started. At point B, the tympanic temperature had risen to 38.5° C. and the patient reported to become uncomfortable. An arm of the patient was placed in the chamber of one embodiment of the device of the present invention. The circulating water was set to 23° C. and pulsating pressure was applied to the arm in sequences of 10 seconds at −40 mmHg and 7 seconds at 0 mmHg. The 40-50° C. warm air and relative humidity of 40% were maintained during treatment. Forty minutes later, the tympanic temperature was reduced to 37.5° C. Thus, the present invention can be used to treat patients with hyperthermia.

Other possibilities envisaged within the present invention are making the pressure chamber 4 more anatomically correct; making a "one size fits all" model; one or multi-piece; the provision of a "door" to put the arm/leg into for easier access, etc. In addition to treating hypothermia, the method may be used on many different clinical problems. Treating ischemic feet is one possibility: Another is treating large leg ulcers to avoid amputation. The possibilities are endless.

The invention claimed is:

1. A method of managing a patient's core body temperature by applying temperature-controlled liquid to a body part of the patient, the method comprising the steps of:
    (a) providing a chamber including liquid, the body part being positioned in the liquid and substantially isolated from conditions external to the chamber;
    (b) warming or cooling the liquid, thereby causing a thermal reaction in which the blood in the body part is warmed or cooled by the liquid;
    (c) alternately (i) applying a negative pressure within the chamber for a pooling period of between 8 and 12 seconds, thereby increasing the volume and velocity of blood that is warmed or cooled in the body part by the liquid and (ii) releasing the negative pressure within the chamber for an emptying period of between 5 and 9 seconds, thereby forcing an increased volume of warmed or cooled blood from the body part to other regions of the patient's body through the patient's circulatory system, the emptying period being different than the pooling period; and
    (d) circulating the liquid in the chamber while alternately applying and releasing negative pressure.

2. The method of claim 1, wherein the pooling period is 5% longer than the emptying period.

3. The method of claim 1, wherein the pooling period is 10% longer than the emptying period.

4. The method of claim 1, wherein the pooling period is 25% longer than the emptying period.

5. The method of claim 1, wherein the emptying period is approximately 7 seconds.

6. The method of claim 1, wherein the pooling period is approximately 10 seconds.

7. The method of claim 6, wherein the emptying period is approximately 7 seconds.

8. The method of claim 1, wherein the body part is positioned within a sleeve inside the chamber, and a negative pressure is applied between the body part and the sleeve to evacuate air between the body part and the sleeve and enhance surface contact between the sleeve and the body part.

9. The method of claim 1, wherein the negative pressure applied within the chamber is approximately −40 mmHg (−5.3 kPa).

10. The method of claim 1, wherein the temperature to which the liquid is adjusted is approximately between 43° C. and 45° C.

11. The method of claim 1, wherein the temperature to which the liquid is adjusted is approximately between 20° C. and 25° C.

* * * * *